United States Patent
Mendoza et al.

(10) Patent No.: US 7,279,309 B2
(45) Date of Patent: Oct. 9, 2007

(54) PROCESS FOR MANUFACTURE OF NEMATODE-EXTRACTED ANTICOAGULANT PROTEIN (NAP)

(75) Inventors: Christine B. Mendoza, San Diego, CA (US); John Lidell, Cleveland (GB); David Moss, North Yorkshire (GB)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 11/313,303

(22) Filed: Dec. 20, 2005

(65) Prior Publication Data

US 2006/0211086 A1    Sep. 21, 2006

Related U.S. Application Data

(63) Continuation of application No. 10/440,475, filed on May 15, 2003, now abandoned.

(51) Int. Cl.
*C12P 21/02*    (2006.01)
*C12N 1/19*    (2006.01)
*C07K 1/18*    (2006.01)
*C07K 1/20*    (2006.01)

(52) U.S. Cl. .................. 435/69.1; 435/255.5; 530/416

(58) Field of Classification Search ..................... None
See application file for complete search history.

(56) References Cited

U.S. PATENT DOCUMENTS 5,612,198 A * 3/1997 Brierley et al. ............ 435/69.9
5,866,543 A * 2/1999 Vlasuk et al. ................. 514/12
6,331,520 B1 * 12/2001 Richardson ................... 514/2

FOREIGN PATENT DOCUMENTS

EP    1 184 393 A1 *    2/2002

OTHER PUBLICATIONS

Cino, "High-Yield Protein Production from *Pichia pastoris* Yeast:" Am. Biotech. Lab, May 1999.
Fausnaugh et al., "Solute and Mobile Phase Contributions to Retention in Hydrophobic Interaction.." J. of Chematog. 359:131-146, 1986.
Gottschalk, "Biotech Manufacturing is Coming of Age" Bioprocess. Int'l. 1(4):54-61, 2003.
Lee et al., "Dose-Response Study of Recombinant Factor VIIa/Tissue Factor Inhibitor Recombinant . . . " Circulation 104(1):74-78, 2001.
Stanssens et al., "Anticoagulant Repertoire of the Hookworm *Ancylostoma caninum*" Proc. Nat'l. Acad. Sci. USA 93:2149-2154, 1996.
Vlasuk et al., "Inhibition of Factor VIIa/Tissue Factor with Nematode Anticoagulant . . . " Trends in Cardiovas. Med. 12(8):325-331, 2002.

* cited by examiner

*Primary Examiner*—Robert A. Wax
(74) *Attorney, Agent, or Firm*—Robins & Pasternak LLP

(57) ABSTRACT

The present invention provides a process for manufacture of purified Nematode-extracted Anticoagulant Proteins (NAPs), wherein the NAP manufactured by the claimed process method is a NAP drug substance that can be formulated as a NAP drug product. The present invention provides NAP drug substances and NAP drug products manufactured by the process disclosed herein. In one embodiment, the present invention provides a process for manufacture of rNAPc2/proline drug substance and rNAPc2/proline drug product, and provides rNAPc2/proline drug substance manufactured by the process disclosed herein.

25 Claims, 8 Drawing Sheets

Recovery Flow Diagram

| Materials and Reagents | Recovery Unit Operations (Process and Equipment) | Controlled and Monitored Conditions |
|---|---|---|
| Buffers: (pH 3.2 ± 0.2)<br><br>500 mM sodium acetate<br><br>50 mM sodium acetate<br><br>50 mM sodium acetate/ 150mM sodium chloride<br><br>50 mM sodium acetate/ 350mM sodium chloride<br><br>Additional Components:<br>17.4 M acetic acid<br>sodium sulfate, anhydrous<br>5N sodium hydroxide<br>2.4 M citric acid<br>0.45 µm filters | Streamline SP XL<br><br><br><br>Equipment:<br>Amersham Biosciences Streamline SP XL matrix contained in an expanded bed glass column body | Load Solution Conductivity: ≤ 9 mS/cm<br>Load Solution pH: 3.1 ± 0.2<br><br>Conditioned Streamline Eluate pH: 3.1 ± 0.2 |
| | | Conditioned Streamline Eluate Conductivity: 100 ± 10 mS/cm |

Purification

PROCESS FOR MANUFACTURE OF NEMATODE-EXTRACTED ANTICOAGULANT PROTEIN (NAP)

RELATED APPLICATIONS

This application is a continuation of U.S. application Ser. No. 10/440,475, filed May 15, 2003 now abandoned, from which application priority is claimed pursuant to 35 U.S.C. §120 and which application is hereby incorporated by reference in its entiretry.

FIELD OF THE INVENTION

The present invention relates to a process for the manufacture of proteins which are anticoagulants in human plasma, and to proteins produced by this process. Specifically, the present invention relates to processes for the manufacture of purified Nematode-extracted Anticoagulant Proteins (NAPs), and relates to purified NAPs manufactured by this process. In particular, the present invention relates to NAP drug substances and NAP drug products, and processes for manufacture thereof.

BACKGROUND OF THE INVENTION

Discovery and purification of therapeutic proteins that have potential value as pharmaceuticals can be carried out in a research laboratory using materials and methods that are not suitable for large-scale commercial production of pharmaceutical products. To generate pharmaceutical products on a commercial scale, biotechnological manufacturing operations must be robust and scalable without compromising product quality (Gottschalk, 2003, *BioProcess Intl* 1(4): 54-61). Manufacturing processes for pharmaceutical products must provide cost-effective methods, improved product yields, sufficient capacity to meet demand and, ideally, should provide process scalability to respond to fluctuations in demand. Manufacturing processes for therapeutic proteins must develop cost-effective methods for producing large quantities of the protein in a functional form, as well as methods for purifying the protein to generate a pharmaceutical product of suitable purity for its intended use.

"Research-scale" methods of protein purification, also known as "laboratory-scale" or "bench-scale" methods, are often closely linked to the methods that were used to discover and characterize the therapeutic protein. Often, a yield of only micrograms or milligrams of purified protein is sufficient for characterizing and sequencing the protein. Even after an expression system for recombinantly producing a therapeutic protein has been developed, such expression systems are not necessarily suitable to produce the protein on a commercial scale. In addition, research-scale purification methods may use organic solvents, strong acids, or other reagents that are not desirable or practical on a commercial scale and sometimes not permitted in the manufacture of pharmaceutical products. Further, these purification methods may use separation methods such as molecular sieving or high-performance liquid chromatography (HPLC) that are powerful purification methods in the laboratory but are not easily scalable to commercial levels of production.

Pilot scale processes, e.g. fermentation volumes of 10 L to 100 L of a host cell expressing a therapeutic protein, are suitable for further study of the production process or to produce sufficient amounts of a therapeutic protein for early clinical studies, but even pilot scale processes are not always scalable to manufacturing the amounts required for later phase clinical studies.

One approach to increasing capacity in biotechnology manufacturing involves extending the production capacity or efficiency of the microbial expression system. A variety of well-established biological "factories" are available for producing therapeutic proteins. However, since the production of a functional protein is intimately related to the cellular machinery of the organism producing the protein, each expression system has advantages and disadvantages for use in large-scale production of pharmaceutical products, depending on the protein. *E. coli* has been the "factory" of choice for the expression of many proteins because it is easy to handle, grows rapidly, requires an inexpensive growth medium, and can secrete protein into the medium which facilitates recovery. However, many eukaryotic proteins produced in *E. coli* are produced in a nonfunctional, unfinished form, lacking glycosylation or other post-translational modifications, as well as formation of proteins with appropriate disulfide bonding and three-dimensional folding. In addition, material produced in *E. coli* can have endotoxin contamination. Similar constraints are often encountered using *Bacillus* species as expression systems. Mammalian cell culture systems provide small amounts of eukaryotic proteins with proper glycosylation and folding, but mammalian cell culture systems are expensive, can be difficult to scale up to commercial production levels, can be unstable, and may require the use of animal serum. Insect cell expression systems are fast, relatively easy to develop, and offer good expression levels for mammalian proteins, but can be expensive, only moderately scalable, and can give inappropriate glycosylation. Yeast expression systems are popular because they are easy to grow, are fast and scalable; however, some yeast expression systems have produced inconsistent results, and it is sometimes difficult to achieve high yields.

One yeast expression system that has shown great promise is the methanotrophic *Pichia pastoris*. Compared to other eukaryotic expression systems, *Pichia* offers many advantages, because it does not have the endotoxin problem associated with bacteria, nor the viral contamination problem of proteins produced in animal cell culture (Cino, *Am Biotech Lab*, May 1999). *Pichia* utilizes methanol as a carbon source in the absence of glucose, using a methanol-induced alcohol oxidase (AOX1) promoter, which normally controls expression of the enzyme which catalyzes the first step in the metabolism of methanol, as a methanol-inducible promoter to drive expression of heterologous proteins. *Pichia's* prolific growth rate makes it easily scalable to large-scale production, although scale-up challenges include pH control, oxygen limitation, nutrient limitation, temperature fluctuation, and safety considerations for the use of methanol (Gottschalk, 2003, *BioProcess Intl* 1(4):54-61; Cino *Am Biotech Lab*, May 1999). Production under current Good Manufacturing Practice (cGMP) conditions is possible with *Pichia pastoris*, at the scale of 1000L fermentations (Gottschalk, 2003, *BioProcess Intl* 1(4):54-61).

Another approach to increasing capacity in biotechnology manufacturing is to improve protein recovery and downstream processing of fermentation products. In downstream processing, processes must be adjustable to accommodate changes and improvements in fermentation titer, media composition, and cell viability, while maximizing the productivity of existing capacity (Gottschalk, 2003, *BioProcess Intl* 1(4):54-61). Recent advances in chromatography and filtration provide significant increases in selectivity, recovery, and offer high capacities and low cycle times to be compatible with large volume and high expression levels of current fed-batch fermentation processes (Gottschalk, 2003, *BioProcess Intl* 1(4):54-61).

Despite great advances in improving biotechnological manufacturing, no global solutions exist for every protein. The manufacturing process for a specific therapeutic protein requires novel and innovative solutions to problems that may be specific for that protein or family of proteins. Likewise, successful commercial applications often rely on a combination of specific properties of the protein or family of proteins, and the production processes used for manufacturing that protein or family proteins as pharmaceutical products.

SUMMARY OF THE INVENTION

The present invention provides a process for the manufacture of purified Nematode-extracted Anticoagulant Proteins (NAPs), and purified NAP drug substances and NAP drug products manufactured by this process. The present invention provides a process for the manufacture of large (commercial scale) quantities of NAP drug substance and NAP drug product. In particular, the present invention provides a process for manufacture of NAP drug substance including the steps of: (a) a fermentation process comprising producing NAP in a suitable host, where at least one sequence encoding NAP is integrated into the genome of the host; (b) a recovery process in which NAP is separated from cells and cellular debris; and (c) a purification process for purifying NAP drug substance away from contaminants. A suitable host is *Pichia pastoris*. The process may further include introducing NAP drug substance into final drug formulation. The process may further include a fill process including bulk filtration of NAP drug substance in final drug formulation, and a fill step that may include dispensing NAP drug substance in final drug formulation in dosage forms to generate NAP drug product, and may further include lyophilization of NAP drug product. The process provided herein can be used to manufacture purified NAP drug substance or NAP drug product from rNAPc2 (AcaNAPc2), rNAPc2/proline (AcaNAPc2/proline), AcaNAP5, AcaNAP6, AcaNAP23, AcaNAP31, AcaNAP42, AcaNAP48, AceNAP5, AceNAP7, AduNAP4, AcaNAP24, AcaNAP25, AcaNAP44, or AcaNAP46.

The present invention provides a NAP drug substance manufactured by the process disclosed herein. The present invention provides a NAP drug substance manufactured using a NAP selected from, but not limited to, rNAPc2 (AcaNAPc2), rNAPc2/proline (AcaNAPc2/proline), AcaNAP5, AcaNAP6, AcaNAP23, AcaNAP31, AcaNAP42, AcaNAP48, AceNAP5, AceNAP7, AduNAP4, AcaNAP24, AcaNAP25, AcaNAP44, or AcaNAP46. In one embodiment, a NAP drug substance of the present invention may be manufactured using rNAPc2/proline. The present invention further provides a NAP drug product manufactured by the process disclosed herein. The present invention provides a NAP drug product manufactured using a NAP selected from, but not limited to, rNAPc2 (AcaNAPc2), rNAPc2/proline (AcaNAPc2/proline), AcaNAP5, AcaNAP6, AcaNAP23, AcaNAP31, AcaNAP42, AcaNAP48, AceNAP5, AceNAP7, AduNAP4 AcaNAP24, AcaNAP25, AcaNAP44, or AcaNAP46. In one embodiment, a NAP drug substance of the present invention is manufactured using rNAPc2/proline.

In accordance with another aspect, the present invention provides a process for manufacture of rNAPc2/proline drug substances and rNAPc2/proline drug products. The present invention further provides rNAiPc2/proline drug substance and rNAPc2/proline drug products manufactured by the process disclosed herein. In particular, the present invention provides a process for manufacture of rNAPc2/proline drug substance including a fermentation process, a recovery process, and a purification process. The process provided herein includes a fermentation process wherein rNAPc2/proline is produced in *Pichia pastoris* having at least one sequence encoding rNAPc2/proline is integrated into the genome, where the fermentation process includes a seed fermentation to grow host cells to a desired cell density and a production fermentation process comprising glycerol batch fermentation, glycerol fed-batch fermentation, methanol adaptation fermentation, and methanol induction fermentation, for up to about seven days. The process provided herein further provides a recovery process including ion exchange expanded bed chromatography to separate rNAPc2/proline from cells and cellular debris. The process provided herein further provides a purification process including hydrophobic interaction chromatography utilizing hydrophobic interaction chromatography media, collecting rNAPc2/proline fractions, at least one ultrafiltration/diafiltration (UF/DF) of rNAPc2/proline fractions, ion exchange chromatography, and collecting rNAPc2/proline fractions from ion-exchange chromatography, wherein the rNAPc2/proline fractions from ion-exchange chromatography contain rNAPc2/proline drug substance. In accordance with one aspect, the process includes controlling temperature for fermentation, in particular maintaining the temperature of the methanol adaptation fermentation at about 28±2° C. for about the first four hours and at about 25±1° C. for the remainder of the methanol adaptation fermentation. In accordance with another aspect, the pH is maintained at about 2.9±0.1 during the methanol adaptation fermentation and the methanol induction fermentation. In one embodiment, the recovery process includes STREAMLINE SP XL ion exchange resin expanded bed chromatography at a pH of about 3.2±0.2, and the purification step includes SOURCE 15PHE hydrophobic interaction chromatography at about pH 3.0±0.1 and SOURCE 15Q ion chromatography, followed by UF/DF of NAP fractions from ion-exchange chromatography.

Further provided is a process for manufacture of rNAPc2/proline liquid drug product including manufacturing rNAPc2/proline drug substance by the process described above, followed by introducing rNAPc2/proline drug substance into final drug formulation, a fill process including bulk filtration and a fill step comprising dispensing rNAPc2/proline in a final dosage form such dispensing into a container or vial to generate rNAPc2/proline liquid drug product, and may further include lyophilization of rNAPc2/proline drug product. The present invention provides rNAPc2/proline liquid drug product manufactured by this process and rNAPc2/proline lyophilized drug product manufactured by this process.

The present invention provides a process for the manufacture of large (commercial scale) quantities of NAP drug substance, in particular rNAPc2/proline drug substance. NAP drug substance manufactured by the process provided herein can be formulated and dispensed as NAP drug product, including as a liquid NAP drug product or as a lyophilized NAP drug product. Also, rNAPc2/proline drug substance manufactured by the process provided herein can be formulated and dispensed as rNAPc2/proline drug product, including as a liquid rNAPc2/proline drug product or as a lyophilized rNAPc2/proline drug product.

This process is suitable for efficient commercial scale production of NAP drug substances and NAP drug products having desired levels of activity and purity. In contrast, previously disclosed methods for purifying NAPs were research-scale methods that were not scaleable for large-scale production of NAPs, and used reagents and materials that are not desirable in production drug substances and drug products. For example, a previously disclosed recovery process consisted of centrifugation to remove the cells. In the previous process, the supenatant was then purified by cation exchange chromatography, gel filtration chromatography (also known as molecular sieving), and finally, reversed-phase chromatography. However, as provided herein, the properties of NAPs, particularly rNAPc2/proline, enabled modifications of the research-scale process to replace the centrifugation step with a scaleable and cleanable method, to eliminate both a difficult-to-scale gel filtration chromatography step and a reversed-phase high pressure liquid chromatography (RP-HPLC) step that involved the use of flammable organic solvent and specialized equipment, and to improve the final product purity. In the process provided herein, an expanded-bed ion exchange chromatography step, in particular, a STREAMLINE SP XL expanded-bed chromatography step, eliminated the multiple unit operations normally utilized for a commercial process recovery step (e.g., a combination of microfiltration and ultrafiltration). As provided herein, the STREAMLINE SP XL step was used to separate the rNAPc2/proline from the cell debris and exchange the product into a buffer suitable for the first purification step. Although the previously disclosed method used gel filtration and reversed phase chromatography, these column steps were replaced in the present invention by hydrophobic interaction chromatography (HIC) and anion exchange chromatography, in particular HIC using SOURCE 15PHE and anion exchange using SOURCE 15Q, which resulted in a significant purification of rNAPc2/proline through the removal of protein and non-proteinacious contaminants. It appears that the relatively low pI of rNAPc2/proline (pI=4.1) and other NAPs may be involved in producing the surprising result that higher binding to the matrix and a higher overall recovery of the product from the HIC step is dependent on performing this chromatography step at a low pH of about 3.2. In addition, process efficiencies resulted from carrying out the steps at about pH 3, starting from later fermentation steps through STREAMLINE chromatography and HIC, which eliminated buffer exchange between steps.

BRIEF DESCRIPTION OF THE DRAWINGS

FIG. 3. depicts a recovery flow diagram showing the materials and reagents used, process and equipment used, and conditions that are controlled and monitored during the recovery process.

DETAILED DESCRIPTION OF THE INVENTION

Figure 1:
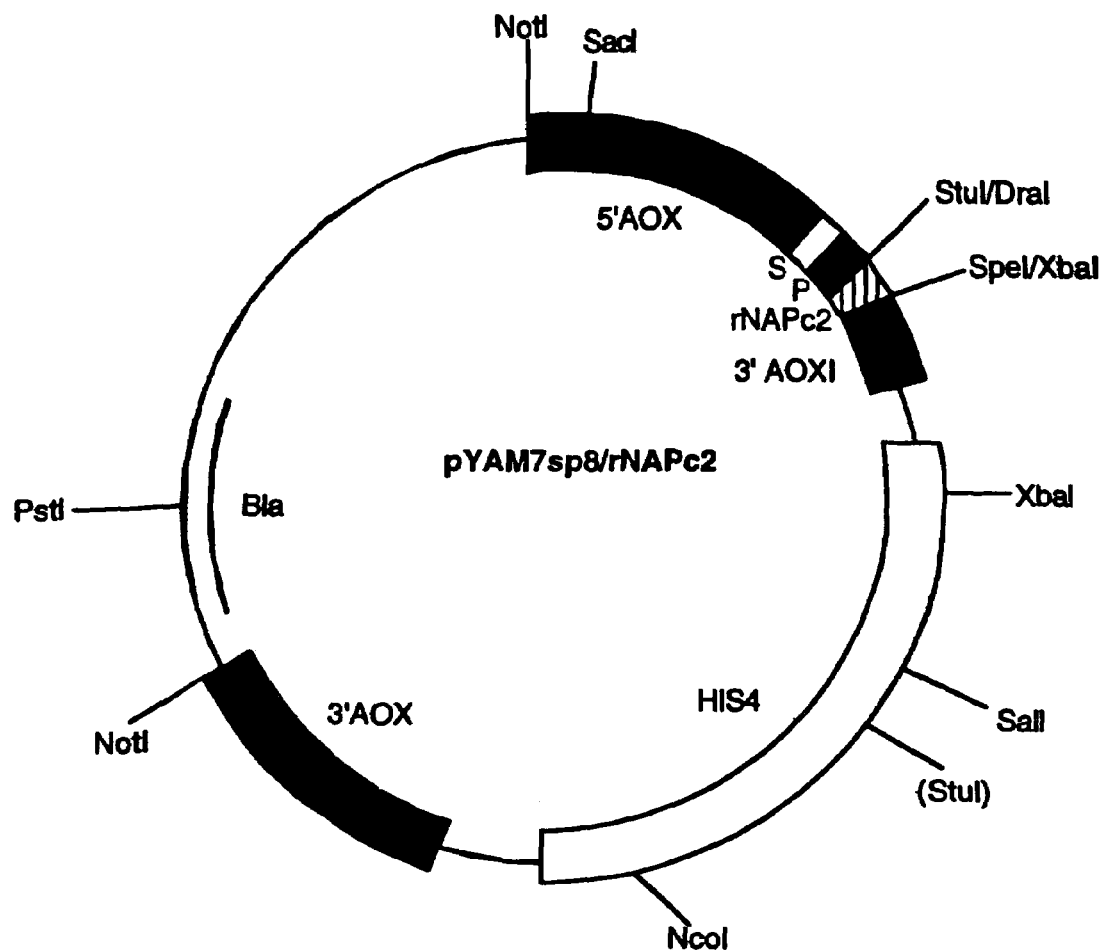
FIG. 1. depicts a vector map of rNAPc2/proline *Pichia pastoris* expression vector pYAM7sp8/rNAPc2/proline used for production of rNAPc2/pro, showing reference points.

The present invention provides a process for manufacture of purified Nematode-extracted Anticoagulant Proteins (NAPs) such as those disclosed in U.S. Pat. Nos. (henceforth, "US") U.S. Pat. Nos. 5,863,894; 5,864,009; 5,866,542; 5,866,543; 5,872,098; and 5,945,275 (the entire contents of each of which is hereby incorporated by reference), wherein NAPs characterized to date have anticoagulant activity and/or serine protease activity. The present invention provides purified NAPs manufactured by the claimed process method, wherein such a purified NAP is a NAP drug substance that can be formulated as a NAP drug product. The present invention may be particularly suited to manufacture of polypeptides including at least one NAP domain. The present invention provides NAP drug substances and NAP drug products manufactured by the process disclosed herein. In one embodiment, the present invention provides a process for manufacture of rNAPc2/proline drug substance and. rNAPc2/proline drug product, and provides rNAPc2/proline drug substance and rNAPc2/proline drug product manufactured by the process disclosed herein.

Nematode-extracted Anticoagulant Proteins (NAPs) are so designated because the first NAP originally isolated was extracted from a nematode, the canine hookworm, *Ancyclostoma caninum*. The term "NAP domain" refers to a sequence believed to have anticoagulant properties. Generally, a NAP domain is an amino acid sequence containing less than about 120 amino acid residues, and containing 10 cysteine residues, as disclosed in U.S. Pat. Nos. 5,863,894; 5,864,009; 5,866,542; 5,866,543; 5,872,098; and 5,945,275. "NAP domain" can also refer to nucleic acids or nucleotide sequences encoding one or more amino acid sequences or polypeptides having NAP domains. Representative NAP domains, NAP amino acid sequences, characteristics broadly defining this family of proteins, and nucleic acid molecules which encode such proteins are disclosed in U.S. Pat. Nos. 5,863,894; 5,864,009; 5,866,542; 5,866,543; 5,872,098; and 5,945,275.

NAP drug substances of the present invention include anticoagulants characterized by inhibiting the clotting of blood, which includes the clotting of plasma. NAP drug substances of the present invention include, among others, those which increase the clotting time of human plasma as measured in both the prothrombin time (PT) and/or activated partial thromboplastin time (aPTT) assays, as disclosed in U.S. Pat. Nos. 5,863,894; 5,864,009; 5,866,542; 5,866,543; 5,872,098; and 5,945,275. One of skill in the art can utilize other assays to determine anticoagulant activity of NAP drug substances. One of skill in the art can likewise utilize other assays to determine other biological activities of NAP drug substances.

The terms "AcaNAPc2" or "rNAPc2" refer to a recombinant protein of the NAP family. The preparation and sequence of AcaNAPc2 is described in U.S. Pat. No. 5,866,542.

The terms "AcaNAPc2/proline," "AcaNAPc2P," "rNAPc2/proline" and "rNAPc2/Pro" refer to a recombinant protein having the amino acid sequence of AcaNAPc2 which has been modified to add a proline residue to the C-terminus of the sequence of AcaNAPc2.

"Drug substance" or "Active Pharmaceutical Ingredient" (API) refers to pharmaceutically active material that can be subsequently formulated with excipients to produce the drug product. Drug substance can be in bulk form. "Drug product" refers to the finished dosage form (e.g., capsule, tablet, liquid product in a vial, lyphophilized powder in a vial) containing drug substance in the final formulation buffer, and usually containing inactive ingredients. Drug product can be a formulated drug substance. "Excipient" refers to inactive ingredients added intentionally to the drug product, where it is understood that excipients do not have pharmacological properties at the quantities used. "Impurity" refers to a component present in a drug substance, API formulation, or drug product that is not the desired product, a product-related substance, or excipient, where it is understood that an impurity may be product-related or process-related. "Degradation products" refers to variants, especially molecular variants, resulting over time from changes in the drug substance or drug product due to light, pH, temperature, water, or reaction with an excipient or a container/packaging/closure system.

"USP" refers to standards set forth in the United States Pharmacopoeia (USP) and the National Formulary (NF) (United States Pharmacopeial Convention, Inc., Rockville Md. (2002), "USP26-NF-21," the entire contents of which are hereby incorporated by reference) and in USP Reference Standards. Additional information can be found at usp.org, or by consulting the USP-NF.

The present invention provides a process that produces high purity NAP drug substance, wherein no raw-material of animal origin is used for any fermentation or purification step. This process is scaleable and suitable to be run at a commercial product scale. The present invention provides a process for manufacture of NAP drug substance and NAP drug product, wherein the process includes fermentation, recovery, purification, filtration, and fill processes. A fermentation process is provided by which NAP is produced in a suitable host, wherein sequences encoding NAP are integrated into the host genome. A recovery process is provided that improves yield and purity of proteins recovered from the fermentation step, wherein the recovery process permits more efficient capture of NAP compared with more conventional methodology such as microfiltration and ultrafiltration. A purification process is provided by which NAP drug substance is purified away from contaminants, wherein desired formulations are achieved using a combination of methods including but not limited to ultrafiltration, diafiltration, hydrophobic interaction chromatography, and ion exchange chromatography. An optional fill process is provided, wherein NAP drug product is introduced into packages and may be lyophilized.

The processes of the present invention are suitable for the manufacture of NAP drug substances and NAP drug products. One of skill in the art can modify the processes as disclosed herein to improve expression, recovery, purification, formulation, or fill of a particular NAP drug substance. In a non-limiting example, one of skill in the art can determine the isoelectric point (pI) of a particular NAP of interest and can make minor adjustments to conditions such as binding capacity or pH of chromatography step to achieve improved purification of the desired NAP drug substance. The present invention provides NAP drug substances purified as disclosed herein from NAPs including but not limited to AcaNAPc2, AcaNAPc2/proline, AcaNAP5, AcaNAP6, AcaNAP23, AcaNAP31, AcaNAP42, AcaNAP48, AceNAP5, AceNAP7, AduNAP4 AcaNAP24, AcaNAP25, AcaNAP46, and AcaNAP44. In particular, the present invention provides rNAPc2/proline. One of skill in the art can identify other NAP proteins suitable for use in the processes disclosed herein to manufacture purified NAP drug substances.

Fermentation

The present invention provides a fermentation process in which NAP is produced in a suitable host. As provided, one or more sequences encoding NAP are integrated in a host genome, and the host produces NAP during the fermentation process. In one embodiment, rNAPc2/proline is produced as a secreted protein by *Pichia pastoris* in a fermentation process as provided herein.

As provided herein, the fermentation process includes a seed fermentation process wherein host cells are grown to a desired cell density and a production fermentation process wherein NAP is produced to a desired titer. A seed fermentation process provides a suitably dense inoculum for a production fermentation process to produce high levels of NAP. The fermentation process provided herein further includes production fermentation to produce high levels of NAP. Production fermentation includes distinct phases: glycerol batch; glycerol fed-batch; methanol adaptation; and methanol induction. The glycerol batch phase builds biomass. In the glycerol-fed batch phase, a glycerol-enriched solution is fed to the culture to increase biomass and repress expression. In the methanol adaptation phase, the glycerol feed is terminated and replaced with a methanol feed which induces the host to produce NAP. In the methanol induction phase, processing conditions at the end of the methanol adaptation phase are maintained in order to maintain production of NAP.

In accordance with one aspect, the pH range for fermentation is controlled to achieve the desired high titer of NAP. In one embodiment, the pH range for fermentation is controlled over a pH range of about 2.9±0.1 pH units during the methanol adaptation fermentation and the methanol induction fermentation. In accordance with another aspect, the temperature for fermentation is controlled. In one embodiment, the temperature of the methanol adaptation phase of the fermentation is held at about 28±2° C. for the first four hours to favor successful adaptation to the methanol feed, and the temperature for the remainder of the methanol adaptation phase, is held at about 25±1° C. to favor a high titer of NAP. In accordance with one aspect, NAP titer continues to increase without detrimental effects on the product for about seven days, which achieves an overall high yield of NAP.

In illustrative embodiments, the fermentation process provided herein has been performed in 15 L, 100 L, 150 L and 1000 L fermentors, and material from 15, 100 and 150 L fermentations has been purified to generate NAP drug substance. In one embodiment, the fermentation process produces rNAPc2/proline at a high titer. In various embodiment, fermentation to produce rNAPc2/proline has been performed in 15 L, 100 L, 150 L and 1000 L fermentors, and rNAPc2/proline drug substance has been purified from 15, 100 and 150 L fermentations.

Recovery

The present invention provides a recovery process to improve yield and purity of NAP proteins from the fermentation step. The recovery process provided herein permits capture of NAP and removal of cells and cellular debris, where the recovery process provided herein is more efficient compared with more conventional methodology such as microfiltration/ultrafiltration. Without wishing to be limited by this theory, the enhanced efficiency of recovery provided herein may result from a combination of aspects of the *Pichia* system, namely that *Pichia pastoris* creates a dense biomass during fermentation. In addition, NAP proteins are relatively small proteins and thus require small-pore-size ultrafiltration membranes, which have slow flux rates resulting in long processing times. In accordance with one aspect, the recovery process utilizes ion-exchange chromatography, including the use of an expanded bed ion exchange chromatography unit to separate NAP from cells and cellular debris and to exchange the product into a buffer suitable for use in subsequent purification steps. In one embodiment, a STREAMLINE SP XL ion exchange resin (Amersham Biosciences) expanded bed chromatography unit is used for recovery of NAP drug substance as described herein. In another embodiment, rNAPc2/proline is separated from cell debris of the host cell expressing rNAPc2 using expanded bed chromatography. In an especially preferred embodiment, rNAPc2/proline is recovered using a STREAMLiNE XL ion exchange unit.

Alternately, the recovery process to efficiently capture NAP from the fermentation step can be carried out using methods other than expanding-bed-ion-exchange cromatography. One of skill in the art can test and evaluate alternate methods for capturing NAP and removing cells and cellular debris including but not limited to affinity chromotography, centrifugation, filtration, differential precipitation, and other methods to be determined.

Purification

The present invention provides a purification process by which NAP drug substance is purified away from contaminants. As provided herein, the purification process includes hydrophobic interaction chromatography, collecting NAP fractions, at least one ultrafiltration and diafiltration (UF/DF) of NAP fractions, ion exchange chromatography, collecting NAP fractions from ion-exchange chromatography, another UF/DF step, and a final filtration. It is understood each step provided in the purification process increases the purity of NAP drug substance, such that one of skill in the art can determine the degree of purity required for a particular use and select the steps and conditions necessary to achieve the desired level of purity of NAP drug substance. Overall process efficiency has been enhanced by maintaining a low pH (about 3) in solution starting from the fermentation broth through the recovery step and first purification step (SOURCE 15PHE hydrophobic interaction chromatography). These steps were specifically designed to be carried out at the same pH, to eliminate pH/buffer exchange steps required in other processes, thereby reducing the time and labor required, as well as reducing potential product losses. These steps are carried out at a pH below about 5, preferably at a pH below about 4, more preferably at a pH of about 3. In one embodiment, hydrophobic interaction chromatography utilizes SOURCE 15PHE hydrophobic interaction chromatography media at about pH 3.0±0.1. As provided herein, the purification process utilizes hydrophobic interaction chromatography to remove contaminants, where use of low pH allows binding of large amounts of NAP to hydrophobic media and use of gradient elution allows separation of closely related impurities. As provided herein, the NAP fraction eluted from hydrophobic interaction chromatography media undergoes ultrafiltration and diafiltration (UF/DF) to concentrate the product and carry out buffer exchange, after which NAP in a suitable buffer is applied to an ion exchange medium to remove most of the remaining protein and non-proteinaceous contaminants, including closely related contaminant. Finally, as provided herein, the NAP fraction collected from ion exchange chromatography, containing highly purified NAP drug substance (API), undergoes UF/DF to concentrate the NAP drug substance and exchange it into the final formulation buffer.

In one embodiment, filtered, conditioned eluate from a STREAMLINE SP XL chromatography step used for NAP recovery is applied to a column of SOURCE 15PHE hydrophobic interaction chromatography media (Amersham Biosciences), at low pH (about 3.0±0.1) wherein large amounts of NAP bind to the column, followed by gradient elution of SOURCE 15PHE, addition of sodium hydroxide to raise the pH to about 5 or higher, and then UF/DF of the eluted NAP fraction, after which the NAP solution is applied to a column of SOURCE 15Q ion chromatography media (Amersham Biosciences) and gradient elution is used to separate NAP drug substance from closely related contaminants. In one embodiment, NAP fractions from in-exchange chromatography contain NAP drug substance. In another embodiment, the purification process is carried out as described above to obtain highly purified rNAPc2/proline drug substance.

As provided herein, solutions containing NAP can undergo various filtration steps to obtain NAP drug substance at desired concentrations or in desired formulations. Additional filtration steps may be included as desired. Accordingly, NAP fractions eluted from chromatography steps can be filtered, concentrated, desalted, or undergo buffer exchange, using ultrafiltration (UF) alone or in combination with diafiltration (DF) or a combination of ultrafiltration and diafiltration (UF/DF). As provided herein, UF/DF can be used to exchange hydrophobic interaction chromatography elution buffer for ion exchange chromatography loading buffer, or exchange ion chromatography elution buffer for a final formulation buffer or bulk drug formulation to be used for the NAP drug product. UF/DF can be carried out using one or more filters. In accordance with one aspect, a single filter (or filter membrane) with a selected molecular weight pore size is used for UF/DF. Alternately, multiple filters can be used as necessary for scale-up. In one embodiment, pH-adjusted NAP fraction from the hydrophobic interaction chromatography step undergoes ultrafiltration using a filter with a 3 kDa MW pore size to achieve a desired concentration, then the pool of NAP-containing retentate is diafiltered against 5 or more volumes of ion exchange loading buffer using the same 3 kDa MW pore size filter membrane until it is determined that the desired buffer conditions have been achieved. In one embodiment, NAP fractions from ion-exchange chromatography undergo at least one final UF/DF. In another embodiment, the NAP fractions from ion exchange chromatography step undergoes UF/DF as described above to exchange NAP drug substance into final drug formulation buffer. In another embodiment, regenerated cellulose ultrafiltration filters with 3 kDa MW pore size are used for ultrafiltration or diafiltration. One of skill in the art can select and evaluate filters or filter membranes that are suitable for, and compatible with, experimental conditions and desired goals.

Bulk Filtration

As provided herein, NAP drug substance in final formulation buffer can be filtered and stored, or undergo further processing steps. In one embodiment, NAP drug substance in final formulation undergoes a fill process. In one embodiment, bulk NAP drug substance is transferred to a suitable sterile environment, e.g., a "Class 100 area" in a manufacturing facility, and filtered into sterile containers. In one embodiment, NAP drug substance is filtered, e.g. using a 0.2 µm filter, into autoclaved containers of suitable material, e.g. containers made of fluorinated ethylene propylene (FEP), ethylene tetrafluoroethylene copolymer (EFTE), or other material that meets requirements of the Food Additives Amendment of the U.S. Federal Food Drug and Cosmetics and USP Class VI designation. In one embodiment, bulk rNAPc2/proline drug product is transferred into a Class 100 area and filtered using a Millipak 0.2 µm filter into autoclaved 1 liter molded Nalgene Tefzel® FEP 1600 series bottle with a molded, linerless, non-contaminating Tefzel®ETFE screw closure, after which the bottles are transferred to a −20±10° C. freezer for storage.

The bulk NAP drug substance may be re-filtered and filled using the same method for final filtration, e.g., the contents of smaller bottles filled as described above can be transferred to a larger container. In one embodiment, the contents of the Teflon FEP bottles containing rNAPc2/proline drug substance as described above are transferred into an autoclaved carboy in a Class 100 area, re-filtered, and filled.

Fill Step

In accordance with one aspect, the present invention further provides a fill step wherein NAP drug substance in final drug formulation is filled into an aseptic vial, container, or other package. The fill step may include additional filtration steps, and may include using a filling suite prior to filling individual vials, containers, or other packages. A fill step may provide a vial of NAP drug product, wherein the NAP drug product is in final dosage form. A liquid fill step may provide a vial of NAP drug product in liquid form. NAP drug product may be used in the form introduced during the fill step, e.g., a unit dose of solution containing NAP drug product. Alternately, the formulation of NAP drug product may be further manipulated after the fill step, e.g., NAP drug product in a vial after a liquid fill step may then be lyophilized. As provided herein, NAP drug substance at the desired final concentration can be filtered into an aseptic filling suit and then filled into individual pre-sterilized vials.

In one embodiment, rNAPc2/proline bulk drug substance (at 12±1.2 mg/mL concentration) is diluted to 3 mg/mL in a solution of 0.2 M alanine and 25 mM sodium phosphate, monobasic, pH 7.0. Diluted rNAPc2/proline is then diafiltered with ≧5 volumes of the alanine/phosphate solution. The rNAPc2/proline solution is removed and the filters are rinsed with the alanine/phosphate solution. Diafiltered rNAPc2/proline solution is then diluted to 2 mg/mL (as measured by the UV assay described below in Examples) with the filter rinses and the alanine/phosphate solution. The 2 mg/mL rNAPc2/proline solution is then diluted with an equal volume of 25 mM sodium phosphate, 8% sucrose, pH 7.0 to achieve a concentration of 1.0±0.1 mg/mL rNAPc2. Finally, the 1 mg/mL formulated rNAPc2/proline solution is filtered using a Millipak 0.2 µm filter (Millipore Corp.) prior to the fill step. rNAPc2/proline drug product at 1 mg/mL is filtered into the aseptic filling suite through two in-line 0.2 µm Millipak filters. The rNAPc2/proline is then filled into individual pre-sterilized 3 cc glass vials and partially stoppered.

As an alternative embodiment, rNAPc2/proline bulk drug substance can be formulated for a liquid drug product. This is described in Example 5.1.

Lyophilization

The present invention provides an optional lyophilization step to produce lyophilized NAP drug product. Following the fill step, NAP drug product in vials or other containers are freeze-dried and then sealed e.g., stoppers in vials are pushed down and the vials are capped. The lyophilized formulation maintains the high purity and sustained stability when NAP drug product is subjected to severe temperature stress, e.g. 28 days at 50° C.

The present invention will be further explained by means of specific examples presented below for the purpose of showing the characteristics of processes for manufacture of rNAPc2/proline and the characteristics of rNAPc2/proline produced by these processes, including data and methods of characterization of purified product. In the following examples, the above-mentioned effects are clarified by disclosing processes for manufacture of rNAPc2/proline drug substance suitable for formulation as a drug product for use in a pharmaceutical composition. These embodiments, however, are set forth to illustrate the invention and are not to be construed as a limitation thereof, the invention being defined by the claims.

EXAMPLES

Example 1

Preparation of Cell Banks for NAP Drug Substance Expression System

Example 1.1 rNAPc2/Proline Expression System

The rNAPc2 gene was cloned into the *Pichia pastoris* expression vector, pYAM7sp8 (Laroche et al, 1994, *Biotechnology* 12:1119-1124) using PCR rescue. The pYAM7sp8 vector (FIG. 1) is a derivative of pHIL-D2 (Despreaux and Manning, 1993, *Gene* 106:35-41). It contains the promoter and transcriptional termination signal of the *Pichia pastoris* AOX1 gene, a secretion signal peptide (a fusion of the *Pichia pastoris* acid phosphatase signal sequence and the pro sequence of a hybrid *S. cerevisiae* α-mating factor), and the HIS4 marker for selecting transfectants.

The PCR primers used to rescue the rNAPc2/proline gene from the phage clone (Jespers et al., 1995, *Biotechnology* 13: 387-382) were:

A8:
(SEQ ID NO:1)
5'GCG <u>TTT AAA</u> GCA ACG ATG CAG TGT GGT G3'

A9:
(SEQ ID NO:2)
5'C <u>GCT CTA GAA</u> GCT TCA TGG GTT TCG AGT TCC GGG ATA TAT AAA GTC3'

These primers add DraI and XbaI sites to the 5' and 3' ends of the rescued DNA fragment, respectively. Underlining indicates nucleotides that hybridize to the template. Primer A9 (SEQ ID NO: 2) also inserts a proline codon just before the termination codon, which converts the coding sequence from one encoding AcaNAPc2 (SEQ ID NO: 3) to one encoding AcaNAPc2/proline (SEQ ID NO: 4). The resulting PCR fragment was digested with DraI and XbaI and cloned into pYAM7sp8 digested with StuI and SpeI. Ligating the blunt ends of pYAM7sp8 (StuI) and the PCR fragment (DraI) resulted in an in-frame fusion of the *P. pastoris* secretion signal peptide to the mature portion of rNAPc2/proline. Ligating the XbaI and SpeI ends of the PCR fragment and pYAM7sp8 resulted in the destruction of the pYAM7sp8 SpeI site.

The *P. pastoris* expression strain was constructed by integrating the expression cassette into the *P. pastoris* genome by homologous recombination. The pYAM7sp8/NAPc2 construct was digested with NotI. The digested plasmid was electroporated into *P. pastoris* GS115 (his4−) cells. Transfectants were screened for methanol utilization phenotype (mut+) and high-level expression of rNAPc2. A single isolate (designated as GS115/AcaNAPc2P-55) was selected for generation of the Master Cell Bank (MCB). The production strain was analyzed by Southern blots that were probed by radiolabeled rNAPc2 or HIS4 genes. These blots showed that multiple copies of the expression cassette were integrated at the 3'-site of the AOX1 gene.

Example 1.2 Master Cell Bank (MCB)

The Master Cell Bank (MCB) was prepared using a prebank of a single colony isolate (GS115/AcaNAPc2P-55). The flask containing YEPD flask medium (bacto peptone, yeast extract, and dextrose) with 2% glucose was inoculated with 0.5 mL of the prebank and grown to an optical density (A550 mm) of 0.5-1.0. The culture was harvested, diluted with glycerol to a final concentration of 15% as a cryopreservative, and frozen in cryovials stored at a temperature below −60° C.

Example 1.3 Manufacturer's Working Cell Bank (MWCB)

A new Manufacturer's Working Cell Bank (MWCB) was manufactured from a vial of the MCB. The MCB vial was used to inoculate a flask containing Yeast Peptone medium (peptone and yeast extract) and 2% dextrose. The flask was incubated at 28±2° C. and 250 rpm until the optical density ($A_{600nm}$) was 17.0±5.0. The culture was harvested, and glycerol as a cryopreservative was added to a final concentration of 9%. Aliquots of 1.1±0.1 mL were filled into 2.0 mL cryovials, frozen and stored at −70±10° C.

Example 1.4 Test Methods Used for Analysis of Master Cell Bank

Host Identification. The rNAPc2/proline cell bank culture was streaked onto Trypticase Soy Agar (TSA) plates and the plates were incubated for growth. The isolate was set up for identification using the Vitek® identification system which utilizes a temperature controlled chamber and photometric sensor unit to monitor changes in turbidity of the isolate suspension which has been inoculated into a Vitek® yeast test card containing substrates for 26 conventional biochemical tests. For the rNAPc2/proline cell bank host identifications, the resulting reaction biopattern was compared to a positive control organism (*Pichia pastoris*, ATCC No. 76273) reaction biopattern.

Viable Cell Concentration. Viable cell concentration of the rNAPc2/proline cell bank was measured by enumeration of viable colony forming units (CFU) by preparation of serial dilutions from three cell bank vials (one each from beginning, middle, and end). The dilutions were plated in triplicate onto TSA plates and incubated CFUs are counted and calculations performed to determine cell concentration as CFU/mL.

Structural Gene Sequence Analysis. The cell bank culture was prepared for gene sequencing by amplifying the rNAPc2/proline gene incorporated into the host genome using the Polymerase Chain Reaction (PCR) technique. The PCR product was purified and the concentration determined. The PCR product was then sequenced using dideoxy chain termination (Sanger) method. The resulting gene sequence of the cell bank was compared to the known DNA sequence of rNAPc2. Identity was confirmed by a 100% match.

Non-Host Contamination Assay. The rNAPc2/proline fermentation broth was tested for non-host contamination by inoculating 100 mL onto each of nine TSA plates. Three plates were incubated at three temperatures (20-25° C., 30-34° C., and 35-39° C.). During th seven day incubation period the plates were inspected for microbial colonies that differ from the characteristic host, particularly noting differences in colony morphology, color and/or colony size. A Gram stain was also performed on the final read plate. Appropriate negative controls were included in the assay.

Example 1.5 Test Methods Used for Analysis of Manufacturer's Working Cell Bank

Host Identification. The rNAPc2/proline cell bank culture was streaked onto Sabouraud Dextrose Agar (SDA) plates and the plates were incubated for growth at 20-25° C. for 7 days. In parallel, a positive control (ATCC strain of *K. pastoris*, an alternate name for *P. pastoris*) was streaked onto SDA plates in the same manner. Selected colonies that grew were then tested by gram staining.

After the incubation, at least two morphologically similar colonies from each SDA plate were selected from the test sample SDA plates and positive control SDA plates. These colonies were subcultured onto separate SDA plates and incubated at 20-25° C. for 7 days. The API 20C AUX test and Gram staining was then performed on growth from each subculture plate. The API test system (bioMérieux SA; Marcy l'Etoile, France) is a manual microbial identification test that contains 20 miniature biochemical tests. The 20C AUX test strip contains 20 biochemical tests specific for identification of yeast. The API testing results for the rNAPc2/proline cell bank test sample were compared to the results obtained for the positive control to confirm identification.

Viable Cell Concentration. Viable cell concentration of the rNAPc2/proline cell bank was measured by enumeration of viable colony forming units (CFUS) by preparation of serial dilutions from two cell bank vials, one vial pulled before freezing the bank and one vial pulled after the bank is frozen. A 100 μL aliquot of each dilution was plated onto duplicate TSA and incubated for 5-7 days. All plates with countable colonies (30-300 CFUs) were counted. Counts obtained from plates of the same test sample dilution were averaged, multiplied by that dilution and divided by the 100 μL aliquot size to report results as CFU/mL.

DNA Sequencing. Total DNA was isolated from the newly created cell bank (test article). The NAPc2/proline gene was amplified by polymerase chain reaction (PCR) using primers homologous to the 5' and 3' sequences of the cloned NAPc2/proline gene. The resulting DNA fragment (approximately 500 bp) was purified using standard methods and used as a template for DNA sequencing using a primer walking strategy performed using the Thermo Sequenase radiolabeled terminator cycle sequencing kit (Amersham Biosciences, Piscataway, N.J.). The sequencing films were read by digitization and the sequence data is assembled and analyzed using Sequencher™ software, version 3.0 (Gene Codes Corp., Ann Arbor, Mich.). The consensus sequence produced from the test article was then compared to the theoretical sequence for the NAPc2/proline gene.

Non-Host Contamination. Prior to freezing the newly created cell bank (test article), a vial was submitted for non-host testing. A sample of the broth was diluted one-thousand fold in saline. Duplicate plates of nine different media types were inoculated with 100 µL of the diluted test sample. In addition, a positive control (ATCC strain of *K. pastoris*, an alternate name for *P. pastoris*) was diluted and inoculated onto plates in the same manner. Another set of plates was not inoculated and designated as the negative controls plates. All plates except SDA were incubated at 30-35° C. for 48-72 hours; the SDA plates were incubated at 20-25° C. for 7 days. The plates were examined for growth after 1, and 2 or 3 days. In addition, the SDA plates were examined for growth after 7 days. Any aberrant colonies were identified by API testing and Gram stain.

After day 2 or 3, at least two morphologically similar colonies from each TSA plate were selected from the test sample TSA plates and positive control TSA plates. These colonies were subcultured onto separate TSA plates and incubated at 30-35° C. for 48-72 hours. The API 20C AUX test and gram staining was then performed on growth from each subculture plate. The API test system (bioMérieux SA; Marcy l'Etoile, France) was a manual microbial identification test that contains 20 miniature biochemical tests. The 20C AUX test strip contains 20 biochemical tests specific for identification of yeast. The API testing results for the test article were compared to the results obtained for the positive control to confirm identification.

Example 2

Manufacture of rNAPc2/Proline Drug Substance

The manufacturing process for production of the rNAPc2/proline drug substance consisted of fermentation, recovery, purification and bulk filtration and fill. The following sections describe the individual unit operations for each stage of the process. Flow diagrams for each unit operation are presented in FIGS. 2-4, where the diagrams summarize the equipment, buffers, components, and input and output parameters. Substitution of equivalent vendors and materials may occur as necessary, while maintaining compliance with International Conference on Harmonization of Technical Requirements for Registration of Pharmaceuticals for Human Use (ICH) Active Pharmaceutical Ingredient (API) Good Manufacturing Protocol (GMP) requirements.

Example 2.1

Fermentation

Figure 2A:
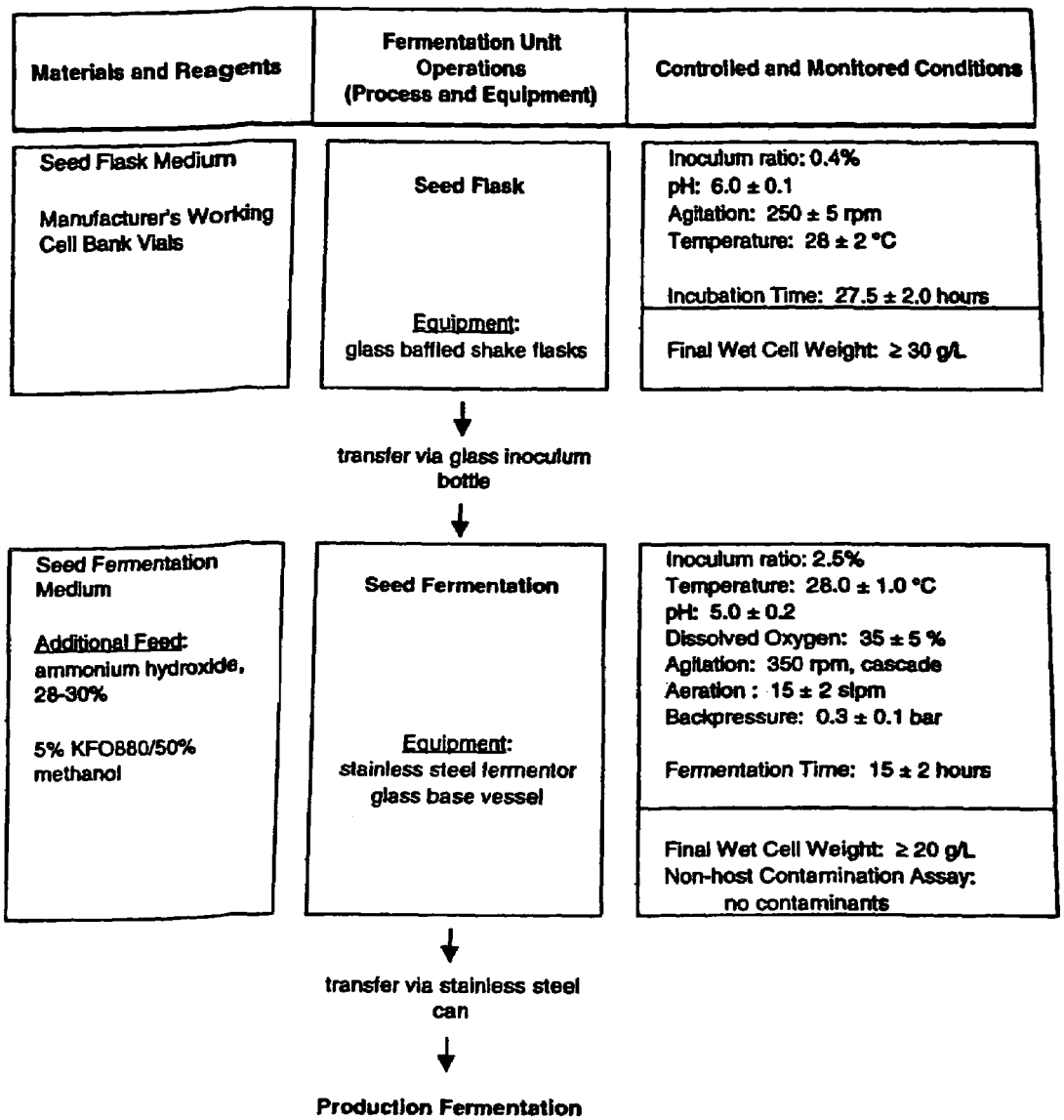
FIGS. 2A. and 2B depict a fermentation flow diagram showing the materials and reagents used, process and equipment used, and conditions that are controlled and monitored for each step in the fermentation process; fermentation begins with preparing the seed flask and continues from seed fermentation through production fermentation.
Figure 2B:
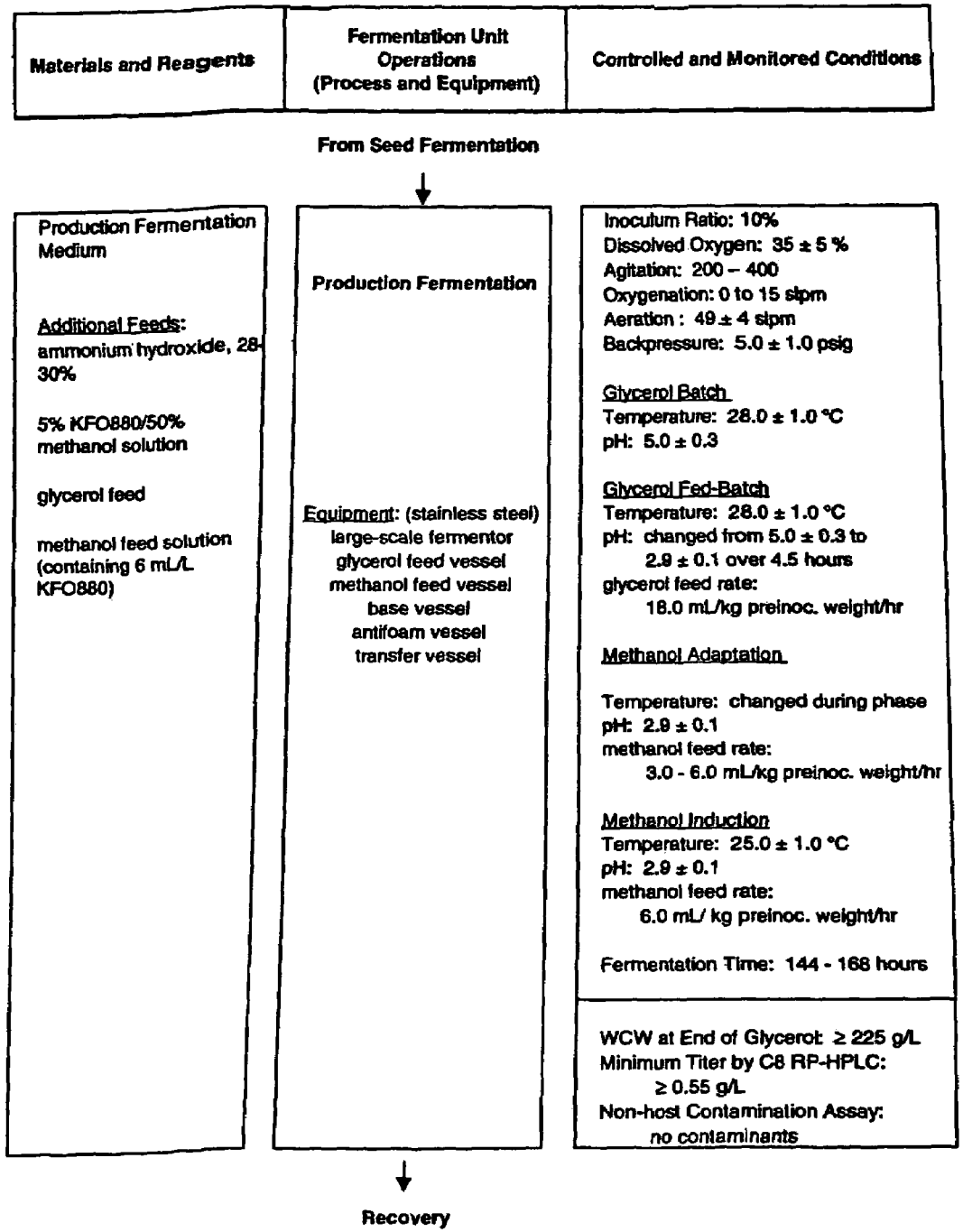

This section describes the fermentation procedures for production of rNAPc2/proline. The rNAPc2/proline protein was produced as a secreted protein by *Pichia pastoris*. The fermentation process for rNAPc2/proline consisted of seed flasks, a seed fermentation, and a production fermentation (FIG. 2, Fermentation Flow Diagram). All media components utilize Purified Water, USP.

Seed Flasks for Seed Fermentation. The purpose of the seed flask unit operation was to provide suitably dense inoculum for the seed fermentation. Three vials of the MWCB were thawed and one milliliter was used to aseptically inoculate each of three two-liter baffled shake flasks containing 250 mL of autoclaved medium at a pH of 6.0±0.1 (Table 1). The flasks were covered and transferred to an incubator shaker at 250±5 rpm and 28±2° C. The flasks were incubated for a period of 27.5±2.0 hours, until the cell density as measured by wet cell weight (WCW) was ≧30 g/L. Once these two parameters were achieved, the contents of two of the flasks were aseptically transferred into an autoclaved inoculum bottle.

TABLE I

Seed Flask Medium

| Components | Concentration |
|---|---|
| Potassium Phosphate, dibasic | 2.30 g/L |
| Potassium Phosphate, monobasic | 11.8 g/L |
| Glycerol | 10 mL/L |
| Yeast Nitrogen Base without amino acids | 13.4 g/L |
| Biotin | 0.4 mg/L |

Seed Fermentation

The purpose of the seed fermentation was to provide a suitably dense inoculum for the production fermentation. The medium for the seed fermentation (Table 2) including PTM4 Trace Salts (Table 3) was transferred into a seed fermentor. The medium was steam sterilized, allowed to cool, and the pH adjusted to 5.0±0.2 with filter-sterilized 28-30% ammonium hydroxide. Filter-sterilized antifoam solution of 5% (v/v) KFO880 in 50% methanol was then added through a septum to a concentration of 0.5 mL/L. When the temperature stabilizes at 28.0±1.0° C., the medium was inoculated with the contents of the seed flask inoculum bottle at a ratio of 2.5%. The culture pH in the fermentor was maintained at 5.0±0.2 with 28-30% ammonium hydroxide. The growth of the fermentation was monitored by measuring the wet cell weight (WCW).

The fermentation was conducted for 15±2 hours and to a final wet cell weight of ≧20 g/L. A portion of the seed fermentation culture was transferred through a steam-sterilized transfer line into an autoclaved inoculum can. A sample of the final seed fermentation was tested for Non-Host Contamination.

TABLE 2

Seed Fermentation Medium

| Components | Concentration |
|---|---|
| Phosphoric acid, 85% | 8.8 mL/L |
| Calcium Sulfate, Dihydrate | 0.93 g/L |
| Magnesium Sulfate, Heptahydrate | 14.3 g/L |
| Potassium Hydroxide | 4.2 g/L |
| Ammonium Sulfate | 5.0 g/L |
| Potassium Sulfate | 18.2 g/L |
| Glycerol, 100% | 7.9 mL/L |
| PTM4 Trace Salts (see Table 3) | 3.0 mL/L |

TABLE 3

PTM4 Trace salts

| Components | Concentration |
|---|---|
| Cupric Sulfate, Pentahydrate | 2.0 g/L |
| Sodium Iodide | 0.08 g/L |
| Sodium Molybdate, Dihydrate | 0.2 g/L |
| Zinc Chloride | 7.0 g/L |
| Ferrous Sulfate, Heptahydrate | 22.0 g/L |
| Boric Acid | 0.02 g/L |
| Cobalt Chloride, Hexahydrate | 0.5 g/L |
| Manganese Sulfate, Monohydrate | 3.0 g/L |
| d-Biotin | 0.2 g/L |
| Sulfuric Acid | 1.0 mL/L |

Production Fermentation

The purpose of the production fermentation was to produce high levels of rNAPc2/proline protein. To achieve this, the culture was grown to a high cell density prior to rNAPc2/proline gene induction. The medium for the production fermentation (Table 4) was prepared in a production fermentor. These media components were dissolved and mixed with purified water USP and then steam sterilized. The tank was cooled to its initial operating temperature of 28.0±1.0° C. A filter-sterilized antifoam solution of 5% (v/v) KF0880 in 50% methanol was then added. The pH was adjusted to its initial operating range of 5.0÷0.3 with filter-sterilized 28-30% ammonium hydroxide. When the initial operating conditions were achieved, the medium was inoculated with the contents of the seed fermentation inoculum can at a ratio of 1 kg inoculum per 10 kg of initially batched medium (pre-inoculation weight).

TABLE 4

Production Fermentation Medium

| Components | Concentration |
|---|---|
| Phosphoric acid, 85% | 8.8 mL/L |
| Calcium Sulfate, Dihydrate | 0.93 g/L |
| Magnesium Sulfate, Heptahydrate | 14.3 g/L |
| Potassium hydroxide | 4.13 g/L |
| Potassium Sulfate | 18.2 g/L |
| Ammonium Sulfate | 5.0 g/L |
| Glycerol, 100% | 23.8 mL/L |
| PTM4 Salts (see Table 3.) | 3.0 mL/L |

The production fermentation consisted of four distinct phases: glycerol batch, glycerol fed-batch, methanol adaptation, and methanol induction. Throughout the fermentation, the dissolved oxygen levels were maintained at approximately 35% by the addition of air at a constant rate and the use of backpressure and variable agitation. If additional oxygen was needed once the maximum agitation was achieved, the air stream was supplemented with oxygen gas. The pH of the culture in the fermentor was maintained with 28-30% ammonium hydroxide. The antifoam solution was periodically added to control foaming.

The first phase of the fermentation, the glycerol batch phase, built biomass. The fermentor was run at 28±2° C. until the glycerol in the media is depleted, as detected by an oxygen spike caused by the cease of metabolism of the glycerol.

This was followed by the glycerolfed-batch phase in which a 50% w/w glycerol solution was fed to the culture at 18.0±1.0 mL/kg pre-inoculation weight/hour for a total of 8.5 hours to increase biomass and repress expression. During the first 4.5 hours of this glycerol feed phase, the pH set point of the culture was lowered from 5.0±0.3 to 2.9±0.1 at a rate of 0.5 pH units each hour, and maintained at this pH for the remainder of the fermentation, i.e., for the duration of the methanol-induced gene induction phase. Temperature was maintained at 28±2° C. throughout this phase. The WCW was ≧225 g/L prior to the end of the glycerol fed-batch phase.

In the methanol adaptation phase, the glycerol feed was terminated and replaced with a methanol feed which induces the organism to produce rNAPc2. The methanol feed (containing 6.0 mL/L KFO880 antifoam) was started at 3.0 mL/kg pre-inoculation weight/hour. The culture was tested for methanol adaptation beginning at 2 hours after initiating the methanol addition. The test for methanol adaptation consisted of briefly terminating the feed and verifying a spike in dissolved oxygen. After the first four hours of methanol addition the temperature was lowered to 25±1° C. over a 2 hour period. After the first four hours of methanol addition and after verification that the culture was utilizing methanol, the methanol feed rate was increased by 1.0 mL/kg pre-inoculation weight/hour. Methanol consumption was measured hourly to ensure that the methanol was being completely depleted, at which point the methanol feed rate was increased by 1.0 mL/kg pre-inoculation weight/hour, up to a final feeding rate of 6.0 mL/kg pre-inoculation weight/hour.

During the methanol induction phase, the processing conditions at the end of the methanol adaptation phase were maintained throughout the remaining fermentation. Beginning at approximately 48 hours of total fermentation time, the production of rNAPc2/proline was monitored by determining the concentration of the broth supernatant, as measured by C8 Reversed-Phase assay. The production fermentor was harvested after 144 to 168 hours in the production fermentor, and after the rNAPc2/proline concentration as measured by the C8 Reversed-Phase assay was ≧0.55 g/L. A sample of the final fermentation was tested for Non-Host Contamination.

The pH was maintained at 2.9±0.1 during the methanol adaptation phase and the methanol induction phase. The fermentation broth has a pH of 2.9±0.1.

Example 2.2

Recovery

This section describes the recovery procedures for rNAPc2/proline production. The recovery process for rNAPc2/proline consisted of an expanded bed chromatography unit operation, as shown in the flow diagram of FIG. 3.

STREAMLINE SP XL Ion Exchange Chromatography

The purpose of the STREAMLINE SP XL ion exchange chromatography step was to separate the rNAPc2/proline from the cell debris and to exchange the product into a buffer suitable for the first purification chromatography step. The medium used to achieve the separation was an expanded bed ion exchange chromatography column of STREAMLINE SP XL resin (Amersham Biosciences).

The fermentation broth (at pH 2.9±0.1) was diluted with purified water until the conductivity is ≦9 mS/cm. The solution was adjusted to a concentration of 150 mM acetate and the pH was adjusted to pH 3.1±0.2 using 17.4 M acetic acid. The load solution was applied to an expanded resin bed that has been equilibrated with 500 mM sodium acetate, pH 3.2 followed by 50 mM sodium acetate, pH 3.2. The column was washed in upflow mode with 50 mM sodium acetate, pH 3.2 and then with 50 mM sodium acetate/150 mM NaCl, pH 3.2. The resin bed was allowed to settle and an additional wash is performed using the 50 mM sodium acetate/150 mM NaCl, pH 3.2 in downflow mode. rNAPc2/proline was eluted by the application of 50 mM sodium acetate/350 mM NaCl, pH 3.2, and rNAPc2/proline concentration was measured by the C8 Reversed-Phase assay.

In preparation for the SOURCE 15PHE purification chromatography step, solid sodium sulfate was added to the STREAMLINE eluate to a final concentration of 0.85 M. The pH was adjusted to 3.1±0.2 using 2.4 M citric acid and the conductivity was verified to be 100±10 mS/cm. The conditioned STREAMLINE eluate was filtered through 0.45 µm filters.

Example 2.3.

Purification

Figure 4A:
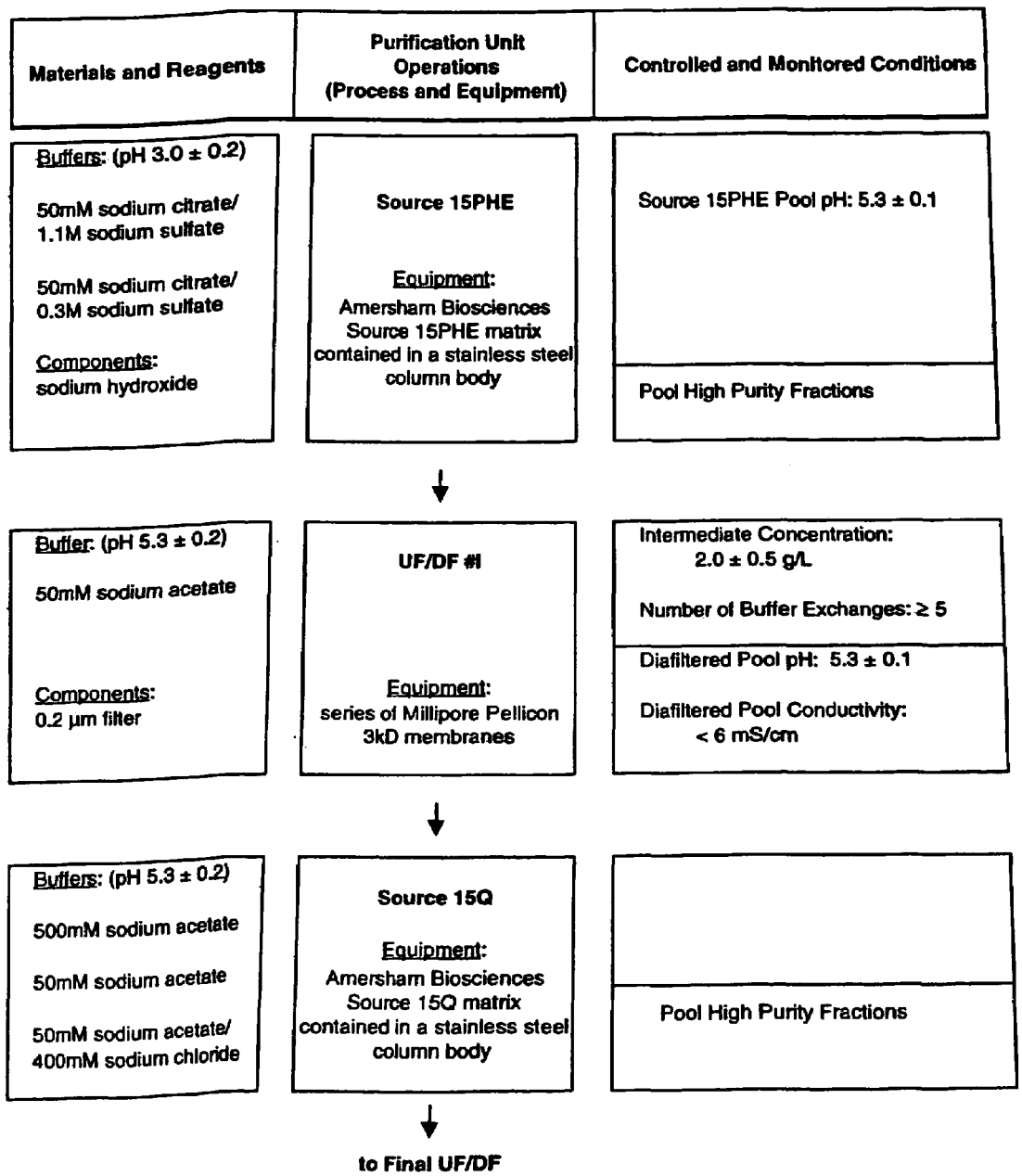
FIGS. 4A. and 4B. depict a purification flow diagram showing the materials and reagents used, process and equipment used, and conditions that are controlled and monitored during the purification process; purification includes the steps of hydrophobic interaction-exchange chromatography on SOURCE 15PHE, ultrafiltration/diafiltration step #1 (UF/DF #1), ion-exchange chromatography on SOURCE 15Q, final UF/DF step, bulk filtration, fill, and storage of purified product.
Figure 4B:
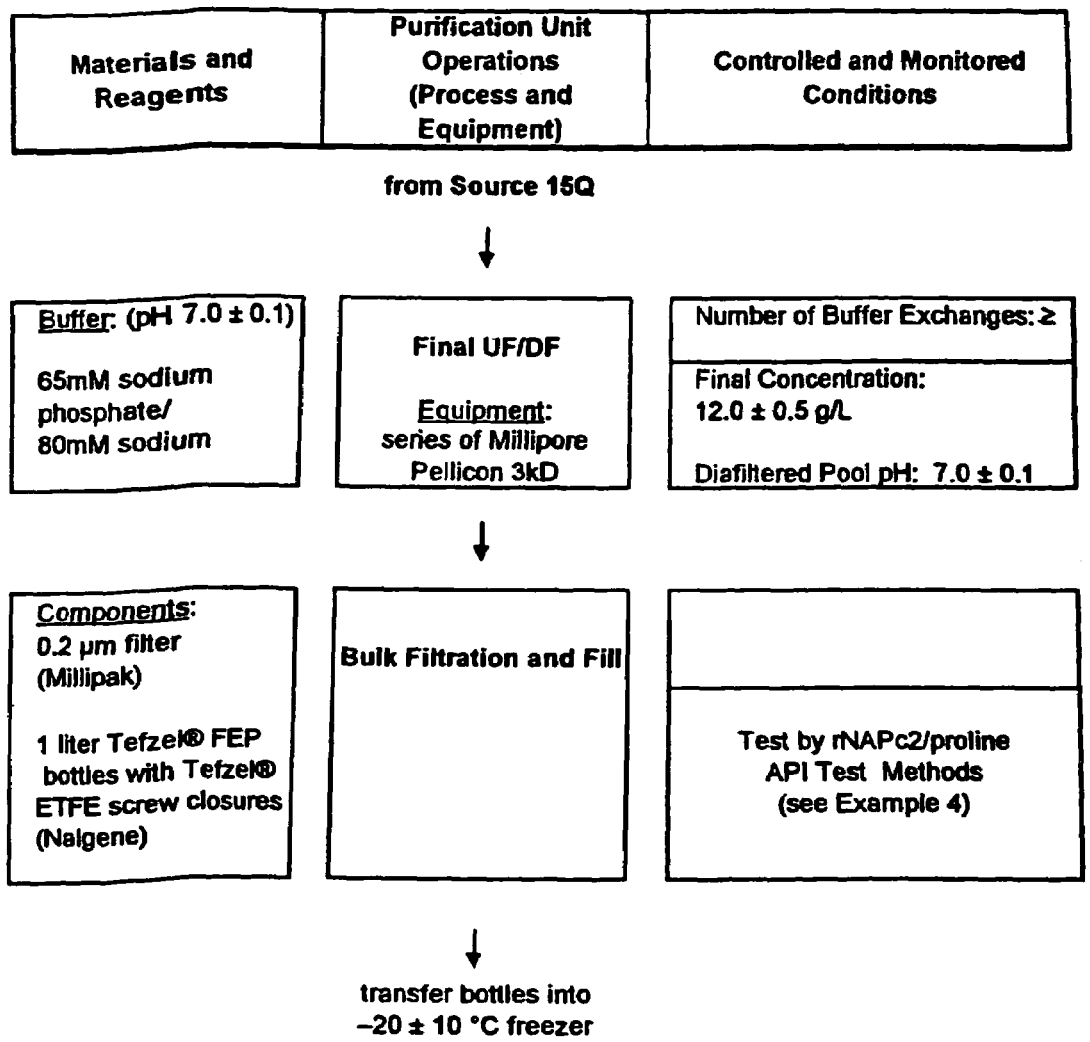

This section describes the purification procedures for rNAPc2/proline production. The purification manufacturing process for rNAPc2/proline consisted of a hydrophobic interaction chromatography step, an ultrafiltration and diafiltration step, an ion exchange chromatography step, followed by an ultrafiltration/diafiltration step, and final filtration and fill of the rNAPc2/proline drug substance, also called the Active Pharmaceutical Ingredient (API), as shown in FIG. 4.

SOURCE 15PHE Hydrophobic Interaction Chromatography The initial purification step partially purified the product by removing some protein and non-proteinaceous contaminants from rNAPc2/proline using a column of SOURCE 15PHE hydrophobic interaction chromatography media (Amersham Biosciences).

The filtered, conditioned STREAMLINE eluate was applied to a SOURCE 15PHE column previously equilibrated with 50 mM sodium citrate/1.1M sodium sulfate, pH 3.0. After loading, the column was washed with the equilibration buffer. The rNAPc2/proline protein was eluted from the column using a 15 column volume gradient from 1.1M to 0.3M sodium sulfate in 50 mM sodium citrate, pH 3.0, followed by a gradient hold of the 0.3M sodium sulfate until the UV absorbance returns to baseline. Fractions were collected across the rNAPc2/proline elution peak and then analyzed by the C18 Reversed-Phase assay. Fractions containing high purity of rNAPc2/proline purity were pooled and tested by the Concentration by UV assay. The pH of the SOURCE 15PHE pool was adjusted to pH 5.3±0.1 by the addition of 5N NaOH.

Ultrafiltration/Diafiltration Step #1 (UF/DF #1)

The purpose of UF/DF #1 was to concentrate the product and to exchange the rNAPc2/proline into the buffer used for the SOURCE 15Q chromatography. Regenerated cellulose ultrafiltration filters of a 3 kD molecular weight pore size were utilized.

The pH-adjusted SOURCE 15PHE pool was concentrated to 2.0±0.5 g/L (as measured by Concentration by UV) on the UF/DF#1 membranes that have been previously equilibrated with 50 mM sodium acetate, pH 5.3. The pool was then diafiltered with ≧5 volumes of 50 mM sodium acetate, pH 5.3, and until the pH was 5.3 ±0.1 and the conductivity was <6.0 mS/cm. The diafiltered UF/DF#1 pool was filtered through a 0.2 μm filter in preparation for loading onto the SOURCE 15Q column.

SOURCE 15Q Ion Exchange Chromatography

The final chromatography unit operation removed most of the remaining protein and non-proteinaceous contaminants from rNAPc2/proline using a column of SOURCE 15Q ion exchange chromatography media (Amersham Biosciences).

The filtered UF/DF#1 pool was applied to the SOURCE 15Q chromatography column previously equilibrated with 500 mM sodium acetate, pH 5.3 followed by 50 mM sodium acetate, pH 5.3. After loading, the column was washed with the 50 mM sodium acetate, pH 5.3 equilibrium buffer. A 20 column volume linear gradient from 0 to 400 mM NaCl in 50 mM sodium acetate, pH 5.3 was applied to the column. Fractions were collected across the elution peak and analyzed by the C18 Reversed-Phase assay. Fractions containing high purity of rNaPc2/proline purity were pooled and tested by the Concentration by UV assay.

Final Ultrafiltration/Diafiltration Step (Final UF/DF)

The purpose of the Final UF/DF was to concentrate the product and to exchange the rNAPc2/proline into the final formulation buffer. Regenerated cellulose ultrafiltration filters of a 3 kD molecular weight pore size were utilized.

The SOURCE 15Q pool was concentrated to 12.0±0.5 g/L (as measured by Concentration by UV) on the Final UF/DF membranes, previously equilibratred with the final formulation buffer, 65 mM sodium phosphate/80 mM sodium chloride, pH 7.0. The pool was then diafiltered with ≧6 volumes of the formulation buffer, and until the pH was 7.0±0.1.

Example 2.4

Bulk Filtration and Fill

The purified rNAPc2/proline API was transferred into a Class 100 area and filtered using a Millipak 0.2 μm filter into autoclaved 1 liter molded Nalgene Tefzel® FEP (fluorinated ethylene propylene) 1600 series bottle with a molded, linerless, non-contaminating Tefzel® ETFE (ethylene tetrafluoroethylene copolymer) screw closure. The bottles were transferred into a −20±10° C. freezer for storage.

The bulk API may be re-filtered and filled using the same method for final filtration. The contents of the Teflon FEP bottles were transferred into an autoclaved carboy in a Class 100 area, re-filtered, and filled. Regarding the storage containers and closures: both FEP and ETFE meet the requirements of the Food Additives Amendment of the U.S. Federal Food Drug and Cosmetics Act. The material met the requirements for USP Class VI designation.

Example 3

In-Process Controls: rNAPc2/proline In-Process Test Methods

Conditions that were monitored, including in-process acceptance criteria, are listed in the process flow diagrams (FIGS. 2-4). Brief descriptions of the In-Process Test Methods are listed below.

rNAPc2 In-Process Test Methods pH. A sample was read using a pH meter that had been calibrated with NIST traceable pH standards immediately prior to testing. The pH of the sample was read at 25±2° C.

Conductivity. The electrolytic components of the solution were measured using a conductivity meter that had been standardized with conductivity standards bracketing the range to be measured. The conductivity of the sample was read at ~25° C.

Wet Cell Weight. Approximately 1.5 mL of fermentation samples were added to tared microcentifuge tubes and centrifuged at 10,000 rpm for approximately 5 minutes. The supernatant from each tube was decanted and the tubes containing the solids were weighed. The wet cell weight was equal to the net weight divided by the original sample volume.

Non-Host Contamination Assay The final broth of the seed and production fermentation samples were tested for non-host contamination by inoculating. 100 μL onto each of nine TSA plates. Three plates were incubated at three temperatures (20-25° C., 30-34° C. and 35-39° C.). During the seven day incubation period the plates were inspected for microbial colonies that differ from the characteristic host, particularly noting differences in colony morphology, color and/or colony size. A Gram stain was also performed on the final read date. Appropriate negative controls were included in the assay.

C8 Reversed-Phase Assay (Concentration and Purity). The supenatant of the production fermentation samples, and STREAMLINE SP XL samples were 0.22 μm filtered and then injected onto a KROMASIL C8, 4.6×250 mm Reversed-Phase column. The column was equilibrated with 22% acetonitrile, 0.1% trifluoroacetic acid (TFA) prior to the sample injection. A linear gradient was then run from 22-28% acetonitrile in 0.1% TFA over twenty minutes at 1 mL/min to elute the rNAPc2/proline material. Standard dilutions of rNAPc2/proline having known concentrations were used to generate a standard curve based upon a linear regression of rNAPc2/proline mg/mL versus peak area. The amount of rNAPc2/proline in any sample was extrapolated from the standard curve and divided by the volume of sample injected to determine the concentration of rNAPc2/proline in the samples. rNAPc2/proline purity was calculated as a percent of the total peak area.

Concentration by UV. The concentration of each purification pool from the SOURCE 15PHE through the Final UF/DF step was determined using its absorbance at 280 nm on a suitably calibrated spectrometer. The instrument was zeroed using the applicable buffer solution prior to running the test samples. Test samples were prepared by diluting within the linear range (between 0.13-1.62 AU). The average absorbance at 280 nm was divided by the extinction coefficient [0.59 AU/cm$^{-1}$(mg/mL)$^{-1}$] and multiplied by the dilution factor to obtain the concentration in mg/mL.

C18 Reversed-Phase Assay (Purity). The purity of the SOURCE 15PHE fractions and pool, UF/DF #1 pool, SOURCE 15Q fractions and pool, and the Final UFDF pool were each analyzed by the C18 Reversed-Phase assay. rNAPc2/proline was separated from other components of a sample by linear gradient Reversed-Phase chromatography. Samples were diluted, if necessary, to approximately 1 mg/mL in cPBS and 30 μL was injected into a WATERS SYMMETRY C18 Reversed-Phase column (5 μm particles, 4.6 mm I.D.×250 mm length, Waters Corp., Bedford Mass.) equilibrated in 78% mobile phase A (0.1% TFA in water) and 22% mobile phase B (0.1% TFA in acetonitrile). The percentage of mobile phase B was then increased linearly to 26% over a twenty minute time period, using a 1 mL/min flow rate. The peaks were monitored by the UV detector at 210 nm. The purity of rNAPc2/proline was calculated by dividing the area of the rNAPc2/proline peak by the total peak area in the chromatogram and expressing that ratio as a percentage.

Example 4 rNAPc2/proline API Test Methods

Appearance, pH, and Concentration: An aliquot of the test article was examined visually for color, clarity and any visible foreign presence. A sample was read using a pH meter calibrated with NIST traceable pH standards immediately prior to testing. The pH of the sample was read at 25±2° C. The concentration of the sample is determined using its absorbance at 280 nm on a suitably calibrated spectrophotometer. The instrument is blanked using a sample diluent prior to running the test samples. Triplicate test samples are prepared by diluting within the linear range (0.13-1.62 AU) established during method validation. The average absorbance at 280 nm is divided by 0.59 AU/cm$^{-1}$ (mg/mL)$^{-1}$ (the extinction coefficient) and multiplied by the dilution factor to obtain the concentration in mg/mL.

Peptide Map: The rNAPc2/proline test articles and an rNAPc2/proline reference standard were reduced and alkylated prior to enzymatic digestion. The rNAPc2/proline was denatured by treatment with a high concentration of guanidine hydrochloride, then reduced with dithiothreitol. The reduced cysteines were then alkylated with iodoacetamide. The reduced and alkylated rNAPc2/proline preparations were digested with 2% w/w trypsin for approximately 16 hours at 37±2° C. The tryptic peptides from each digested rNAPc2/proline protein sample were then separated by reversed-phase chromatography to generate a fragment pattern in the form of a chromatogram or "fingerprint". The sample elution profile was compared visually to the standard elution profile using the peak retention times. The profiles must be comparable, with no new or deleted peaks.

SDS-PAGE Coomassie (Identity/Purity): Test samples, rNAPc2/proline reference standard and a rNAPc2/proline intensity marker were diluted, with and without a reducing agent, using Novex NUPAGE® LDS Sample Preparation Buffer (pH 8.4) to a final concentration of 0.5, 0.5, and 0.005 mg/mL, respectively. A mixture of protein standards (Novex Mark 12®) was diluted per manufacturer's instructions. The reduced samples were heated for five minutes at 95±2° C. Reduced and unreduced samples were run on separate gels. Ten μg sample loads of the reference standard and test sample, a 0.1 μg sample load of the intensity marker (1% of sample load), and the appropriate mass of the Mark 12 standard were analyzed by electrophoresis on a Novex NuPAGE® precast 4-12% acrylamide Bis-Tris gel at pH 6.4. The gels were stained with Novex colloidal Coomassie blue stain. To confirm identity, the main band was compared visually to the reference standard and to the mixture of protein standards. The intensity of any impurity bands was compared visually to the 1% intensity marker band. Any impurity band greater than the marker was reported. If no impurity band greater than the marker was present, the purity was reported as being comparable to reference. Note that the rNAPc2/proline band did not appear at the expected molecular size. Because of its non-spherical shape, rNAPc2/proline ran at a larger apparent molecular size. The rNAPc2/proline band ran between the 21.5 and 31 kDa standards in non-reduced gels while the rNAPc2/proline band ran with the 21.5 kDa standard in reduced gels. (Novex products are from Invitrogen Corp., Carlsbad Calif.)

C18 Reversed-Phase: rNAPc2/proline was separated from other components of a sample by linear gradient reversed-phase HPLC. The purity of rNAPc2/proline was reported as the ratio of the area of the rNAPc2/proline peak divided by the total peak area in the chromatogram, expressed as a percentage. Thirty μL volumes of sample dilutions at approximately 1 mg/mL in cPBS were injected into a Waters Symmetry C18 Reversed-Phase column (5 μm particles, 4.6 mm I.D.×250 mm length, Bedford Mass.) equilibrated in 78% mobile phase A (0.1% TFA in water) and 22% mobile phase B (0.1% TFA in acetonitrile). The percentage of mobile phase B was then increased linearly to 26% over a twenty minute time period, using a 1 mL/min flow rate. The peaks were monitored by UV detector at 210 nm.

Endotoxin: Endotoxin measurements were performed per USP method.

Bioactivity: rNAPc2/proline prolonged the clotting time of human plasma initiated by the addition of thromboplastin in a concentration-dependent manner. The anticoagulant effect of rNAPc2/proline on the clotting of human plasma was directly measured in an automated Prothrombin Time (PT) Clotting Assay using rabbit brain thromboplastin (tissue factor, Simplastin-Excel) to initiate clotting. Both rNAPc2/proline reference standard and rNAPc2/proline sample were diluted to 1035 nM in assay buffer. The test instrument (Coag-A-Mate® MAX, Organon Teknika, now owned by bioMérieux, Durham N.C.) then made a set of dilutions in human plasma from the starting preparation and measured the resulting clotting times (CTs) in seconds. Curves were defined by linear regression fit of the log CTs of the rNAPc2/proline versus the dilution concentrations. The bioactivity of the test article was then calculated as the ratio of the slope of the curve of the test article to the slope of the curve of the reference standard times the activity of the reference standard.

Bioburden: The Total Aerobic Count (TAC) and the Total Yeast/Mold Count (TYMC) in the sample was determined by filtering two 10 mL aliquots through separate 0.45 µm cellulose-ester membrane filters. The filter membranes were prepared and one was incubated on a TSA agar plate at 30-35° C. for 48-72 hours and the other on an SDA agar plate at 20-25° C. for 5-7 days. After the incubation period, the colony forming units (CFU) on both agar types were enumerated. The combined number of CFU per 10 mL sample were reported.

Residual DNA: The Threshold Total DNA assay (Molecular Devices Corp. Sunnyvale Calif.) was specific for single-stranded DNA. It had three stages. In the reaction stage, single stranded DNA reacted with two binding proteins in the labeling reagent. One binding protein was a high affinity, single stranded DNA binding protein (SSB), from $E.\ coli$, conjugated to biotin. Streptavidin, also present, bound tightly to the biotin on the SSB conjugate. The other binding protein was a monoclonal anti-DNA antibody against single-stranded DNA, conjugated to the enzyme urease. These binding proteins formed a complex with DNA, in solution, at 37° C.

The separation stage occurred on the Threshold Workstation. The DNA complex was filtered through a biotin coated nitrocellulose membrane. The biotin on the membrane reacted with streptavidin in the DNA complex, capturing the complex. A rapid wash step removed nonspecific enzyme from the membrane. For the detection stage, the stick (containing a biotin coated nitrocellulose membrane) was placed in the Threshold Reader, which contains the substrate urea. The enzymatic reaction changed the local pH of the substrate solution. A silicon sensor recorded a change in the surface potential which is proportional to the pH change. The Threshold Workstation, the computer and the Threshold Software monitored surface potential changes at each measurement site. The computer analyzed these kinetic measurements and quantitates the results, using a previously generated standard curve. Threshold Software computed the concentration of each sample in picograms of DNA.

Size Exclusion: rNAPc2/proline was separated from other components of a sample by size exclusion chromatography on the basis of differences in molecular size. The identity of rNAPc2/proline was confirmed by comparing mean Retention Time (RT) of the three sample replicates with five system suitability standards. The % RT must be 97.0 to 103.0%. The purity of rNAPc2/proline was calculated by dividing the area of the rNAPc2/proline peak by the total peak area in the chromatogram and expressing this as a percentage. Sample dilutions were prepared in cPBS to a nominal concentration of about 1 mg/ml and injected onto a Size Exclusion column (Superdex 75 10/30, Amersham Biosciences). Flow rate was maintained at 0.5 mL/min. The peaks were monitored by UV detection at 210 nm.

Molecular Weight by Mass Spectrometty. The Molecular weight was determined by electrospray mass spectrometry using a VG BIO-Q (QUATTRO II Upgrade) quadrupole mass spectrometer (manufactured by Micromass, Danvers, Mass., currently owned by Water Corp., Bedford, Mass.). The sample was diluted to approximately 1 mg/mL with 0.1% aqeous trifluoroacetic acid and injected onto a pre-washed Trap Cartridge to desalt it. The cartridge was then eluted through the injection port onto the spectrometer.

N-Terminal Sequencing: The test article was sequenced through 15 residues from the N-terminus using the PROCISE N-Terminal Sequencing System (Applied Biosystems, Foster City, Calif.). A β-lactoglobulin calibration standard was sequenced through 15 residues before and after the test article. Cys (cysteine) residues are not observed on the PROCISE system. The obtained sequence is compared to the theoretical sequence of the test article.

Example 5

Manufacture of rNAPc2/Proline Drug Product

Example 5.1

Manufacture of Liquid Drug Product

Figure 5:
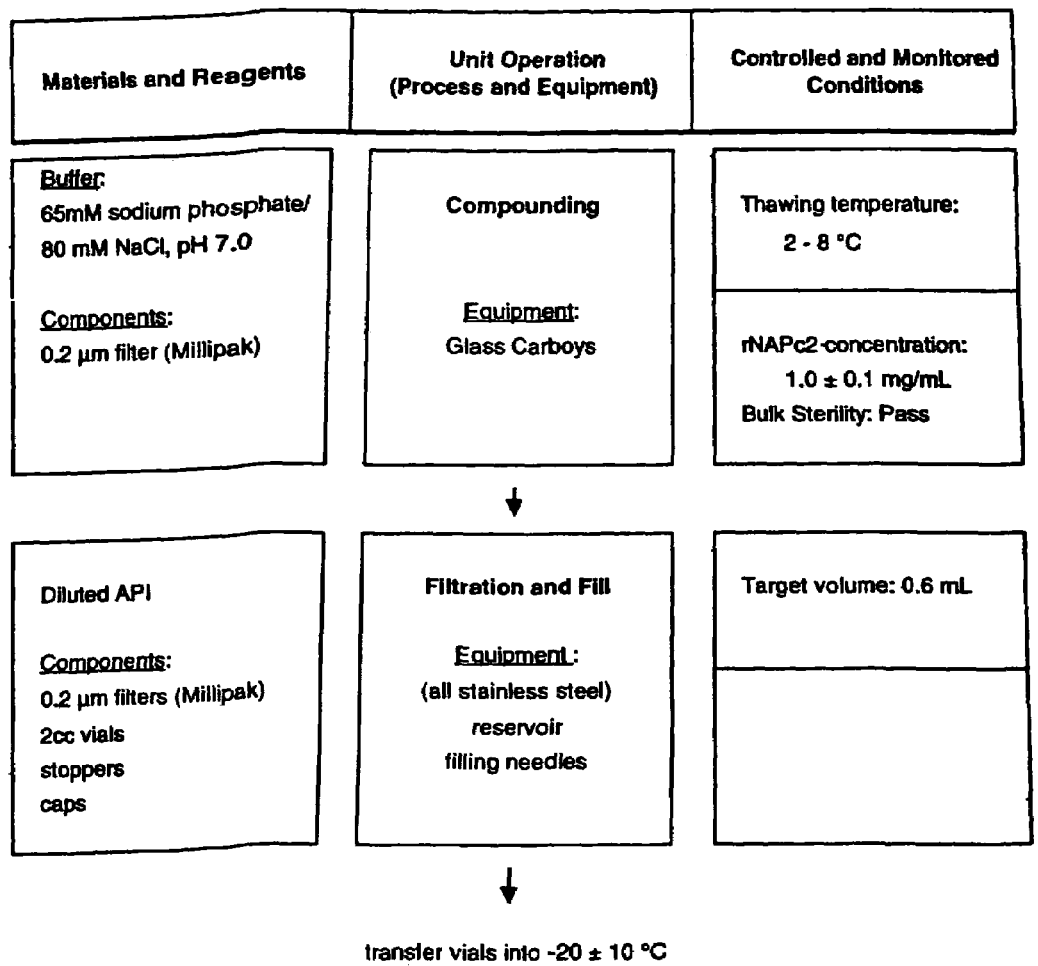
FIG. 5. depicts a liquid drug product flow diagram showing the materials and reagents used, process and equipment used, and conditions that are controlled and monitored during the process of making liquid drug product. This process includes a compounding step, a filtration and fill step, and transfer of vials with liquid drug product into storage.
Figure 6:
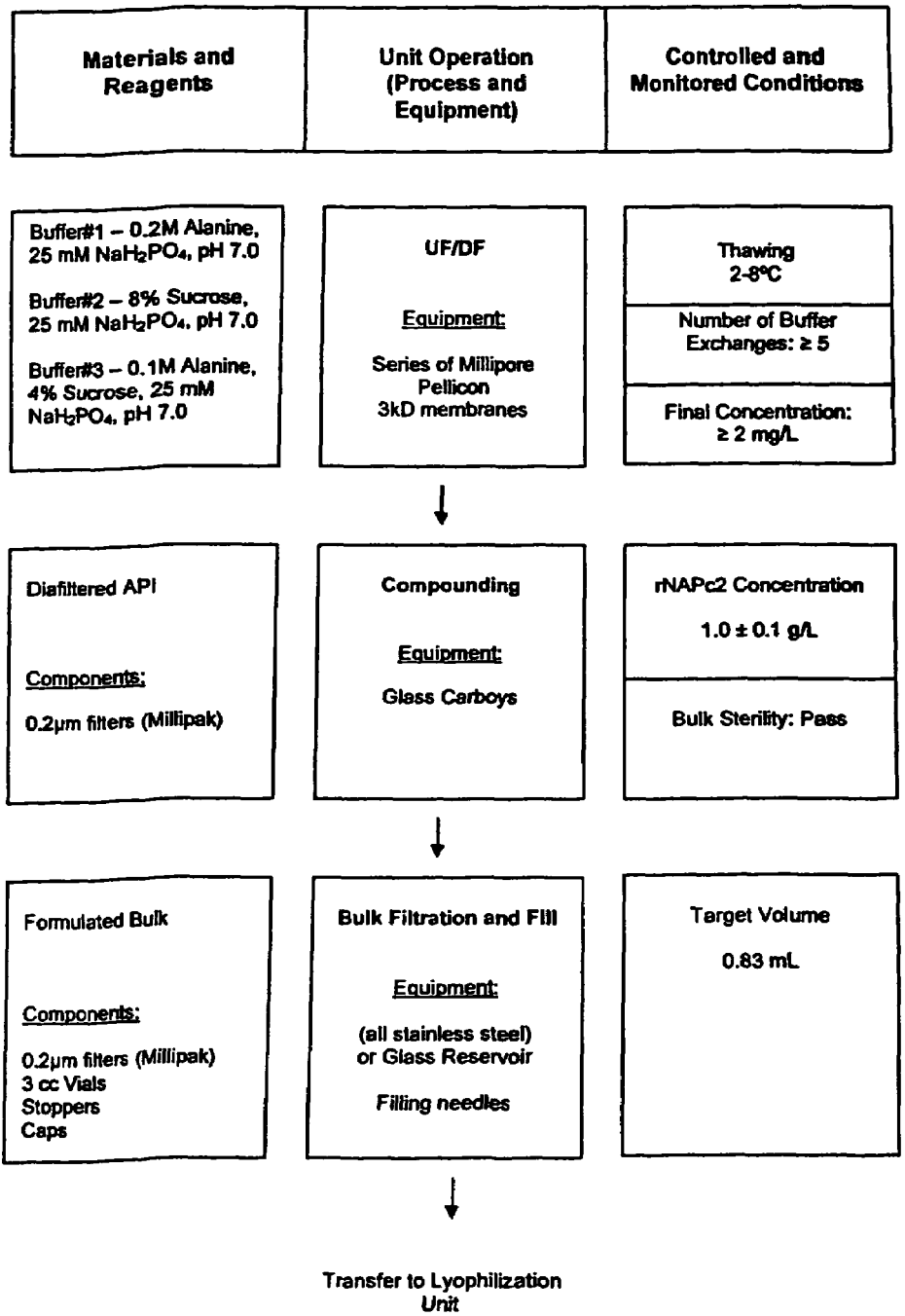
FIG. 6. depicts a lyophilized drug product formulation flow diagram showing the materials and reagents used, process and equipment used, and conditions that are controlled and monitored during the process of formulating lyophilized drug product. The process includes a UF/DF step, a compounding step, a bulk filtration and fill step, and transfer to the lyophilization unit.

The rNAPc2/proline liquid drug product manufacturing process is outlined in FIG. 5, the drug product flow diagram. Frozen rNAPc2/proline API was removed from −20° C. storage and thawed at 2-8° C. Once thawed, the API was transferred to the compounding area for pooling and mixing. To produce the drug product, the API was diluted with 65 mM sodium phosphate/80 mM NaCl, pH 7.0 to a final concentration of 1.0±0.1 mg/mL as measured by the Concentration by UV assay (described above). This dilution was performed in steps with in-process concentration measurements to ensure that the specified concentration was achieved. The diluted API was then filtered through a 0.2 µm Millipore Millipak filter and placed in short term storage at 2-8° C.

For the fill step, the diluted API was filtered into the aseptic filling suite through two in-line 0.2 µm Millipore Millipak filters. Samples were taken for Bulk Sterility testing. The diluted API was then filled into 2 cc pre-sterilized vials that are immediately stoppered and capped. The target volume in the vials was 0.6 mL.

Prior to storage, vials were 100% visually inspected under controlled conditions utilizing lighting and backgrounds designed to illuminate the vials and product so that defective vials, or vials containing visible particulates can be easily detected and removed from the lot. Vials were then loaded into labeled storage trays and held in short term storage at 2-8° C. and long term storage at −20±10° C. Table 5 lists the composition per vial of rNAPc2/proline liquid drug product.

TABLE 5 rNAPc2/proline Liquid Drug Composition

| Material Name | Grade | Amount per vial |
|---|---|---|
| rNAPc2/proline | N/A | 0.6 ± 0.06 mg |
| Dibasic Sodium Phosphate, Heptahydrate | USP | 6.4 mg |
| Sodium Phosphate, Monobasic, Monohydrate | USP | 2.1 mg |
| Sodium Chloride | USP | 2.8 mg |
| Water For Injection | USP | q.s. to 0.6 mL |
| Phosphoric Acid | NF | as needed to adjust pH to 7.0 ± 0.1 |
| 1N Sodium Hydroxide in WFI | made from NF grade pellets | as needed to adjust pH to 7.0 ± 0.1 |

Example 5.2

Manufacture of Lyophilized Drug Product

A solution of rNAPc2/proline Bulk Drug Substance (at 12±1.2 mg/mL concentration, in 65 mM sodium phosphate/80 mM sodium chloride at pH 7.0±0.1) was diluted to 3 mg/mL in a solution of 0.2 M Alanine and 25 mM sodium phosphate monobasic, pH 7.0. The diluted rNAPc2/proline was then buffer exchanged with the alanine/phosphate solution. The rNAPc2/proline solution was then diluted to 2 mg/mL (as measured by the Concentration by UV assay) with the alanine/phosphate solution. The 2 mg/mL rNAPc2/proline solution was then diluted with an equal volume of 25 mM sodium phosphate, 4% sucrose, pH 7.0, to achieve a concentration of 1.0±0.1 mg/mL rNAPc2. Finally, the 1 mg/mL formulated rNAPc2/proline solution was filtered using a 0.2 μm filter.

For filling, the 1 mg/mL rNAPc2/proline solution was filtered through a 0.2 μm filter. The rNAPc2/proline was then filled into individual pre-sterilized 3 cc glass vials and partially stoppered. The vials were then freeze dried in a lyophilizer. After lyophilization, the stoppers were pushed down and the vials are capped. The lyophilized formulation maintains the high purity and sustained stability when NAP drug product is subjected to severe temperature stress, e.g. 28 days at 50° C. Table 6 lists the composition per vial of rNAPc2/proline lyophilized drug product.

TABLE 6 rNAPc2/proline Lyophilized Drug Composition

| Material Name | Grade | Amount per vial |
|---|---|---|
| rNAPc2/proline | N/A | 0.83 mg |
| Alanine | USP | 7.5 mg |
| Sodium Phosphate, Monobasic, Monohydrate | USP | 2.9 mg |
| Sucrose | USP | 3.3 mg |
| Water For Injection | USP | q.s. to 0.83 mL |
| 1N Sodium Hydroxide in WFI | made from NF grade pellets | as needed to adjust pH to 7.0 ± 0.1 |

Example 6

Prediction of NAP Protein Isoelectric Points.

The isoelectric point (pI) of various NAPs was determined to confirm that the process disclosed herein is suitable to manufacture NAP drug substances. Sequences of NAP proteins disclosed in U.S. Pat. No. 5,866,542 were calculated by pI prediction programs. Table 7 presents the pI of NAP proteins disclosed in U.S. Pat. No. 5,866,542 as calculated by ProtParam and Atalier BioInformatique. ProtParam, which uses ExPASy (Expert Protein Analysis System) developed by the Swiss Institute of Bioinformatics (SIB), is found at us.expasy.org/tools/protparam.html, hosted by North Carolina Supercomputing Center (NCSS). Atalier BioInformatique (aBi) is found at up.univmrs.fr/~wabim/d abim/compo-p.html, hosted by the UniversitéAix-Marseille I.

TABLE 7

Predicted pI of NAP Proteins

| Sequence Name | pI calculated by ProtParam | pI calculated by Atalier BioInformatique |
|---|---|---|
| AcaNAP5 | 4.32 | 4.10 |
| AcaNAP6 | 4.25 | 4.03 |
| AcaNAPc2 | 4.31 | 4.10 |
| AcaNAPc2/proline | 4.31 | 4.10 |
| AcaNAP23 | 4.54 | 4.30 |
| AcaNAP24 | 4.72 | 4.45 |
| AcaNAP25 | 4.72 | 4.48 |
| AcaNAP31, 42, 46 | 4.28 | 4.07 |
| AcaNAP44 | 4.74 | 4.48 |
| AcaNAP48 | 4.34 | 4.13 |
| AceNAP5 | 4.49 | 4.25 |
| AceNAP7 | 4.62 | 4.37 |
| AduNAP4 | 4.55 | 4.33 |
| HpoNAP5 | 7.62 | 7.50 |

---

What is claimed is:

1. A process for producing a nematode-extracted anticoagulant protein (NAP) comprising:
    (a) culturing host cells encoding a NAP selected from the group consisting of rNAPc2 and rNAPc2/proline under conditions that result in expression of the NAP;
    (b) recovering NAP from said host cells in a recovery process that does not use centrifugation to remove cells and comprises separating NAP from said host cells and cellular debris to produce a recovered NAP preparation, wherein said recovery process comprises expanded-bed cation exchange chromatography; and
    (c) purifying a NAP from said recovered NAP preparation in a purification process that does not use reversed-phase high pressure liquid chromatography and that comprises performing hydrophobic interaction chromatography, wherein said recovering and purifying with hydrophobic interaction chromatography are conducted at a pH below pH 4.

2. The process of claim 1, wherein the purification process further comprises introducing the purified NAP into a final drug formulation.

3. The process of claim 2, further comprising performing a fill process on the final drug formulation to produce a NAP drug product.

4. The process of claim 1, wherein the NAP is rNAPc2/proline.

5. The process of claim 2, wherein the NAP is rNAPc2/proline.

6. The process of claim 1, wherein the host is *Pichia pastoris*.

7. The process of claim 1, wherein the purification process comprises collecting NAP fractions from the hydrophobic interaction chromatography, performing at least one ultrafiltration/diafiltration (UF/DF) on the NAP fractions to provide a NAP solution, performing anion exchange chromatography on the NAP solution, and collecting NAP fractions from the anion exchange chromatography, wherein the NAP fractions contain NAP.

8. The process of claim 7, wherein the hydrophobic interaction chromatography is performed at about pH 3.0±0.1.

9. The process of claim 7, further comprising performing at least one final UF/DF of fractions from the anion exchange chromatography.

10. The process of claim 9, wherein the UF/DF exchanges the NAP into a final drug formulation buffer to generate a NAP drug product.

11. The process of claim 3, wherein the fill process comprises bulk filtering the NAP in the final drug formulation.

12. The process of claim 11, further comprising a fill step of dispensing NAP in dosage form to produce a NAP drug product.

13. The process of claim 12, wherein the fill process further comprises lyophilizing the NAP drug product.

14. A process for producing an rNAPc2/proline comprising:
(a) providing *Pichia pastoris* host cells encoding rNAPc2/proline;
(b) fermenting said host cells in a fermentation process that comprises a seed fermentation to grow host cells to a desired cell density and a production fermentation process that comprises in sequential order glycerol batch fermentation, glycerol fed-batch fermentation, methanol adaptation fermentation, and methanol induction fermentation, for up to about seven days, wherein said fermenting is conducted at a pH below pH 4;
(c) recovering an rNAPc2/proline substance from said fermented host cells in a recovery process that does not use centrifugation to remove cells and that comprises cation exchange expanded bed chromatography to separate rNAPc2/proline from cells and cellular debris, wherein said recovering is conducted at a pH below pH 4; and
(d) purifying rNAPc2/proline from the recovered rNAPc2/proline substance in a purification process that does not use reversed-phase high pressure liquid chromatography and that comprises performing hydrophobic interaction chromatography utilizing hydrophobic interaction chromatography media wherein said hydrophobic interaction chromatography is conducted at a pH below pH 4, collecting rNAPc2/proline fractions from said hydrophobic interaction chromatography, performing at least one ultrafiltration/diafiltration (UF/DF) on the rNAPc2/proline fractions to provide an rNAPc2/proline solution, performing anion exchange chromatography on the rNAPc2/proline solution, and collecting rNAPc2/proline fractions containing the rNAPc2/proline from the anion exchange chromatography.

15. The process of claim 14, further comprising controlling temperature for fermentation.

16. The process of claim 15, comprising maintaining the temperature of the methanol adaptation fermentation at about 28±2° C. for about the first four hours and at about 25±1° C. for the remainder of the methanol adaptation fermentation.

17. The process of claim 14, comprising maintaining the pH at about 2.9±0.1 during the methanol adaptation fermentation and the methanol induction fermentation.

18. The process of claim 14, wherein the cation exchange resin expanded bed chromatography is performed at a pH of about 3.2.±0.2.

19. The process of claim 14, wherein the hydrophobic interaction chromatography is performed at about pH 3.0±0.1.

20. The process of claim 14, further comprising performing at least one final UF/DF of fractions from the anion exchange chromatography.

21. The process of claim 14 further comprising: (i) introducing the purified rNAPc2/proline into a final drug formulation, (ii) performing a fill process comprising bulk filtration of the rNAPc2/proline in the final drug formulation, and (iii) performing a fill step comprising dispensing rNAPc2/proline in dosage form into a container to generate an rNAPc2/proline liquid drug product.

22. The process of claim 21 further comprising lyophilizing the rNAPc2/proline liquid drug product in the container.

23. A process for producing a nematode-extracted anticoagulant protein (NAP) selected from the group consisting of rNAPc2 or rNAPc2/proline, said process consisting essentially of:
(a) providing *Pichia pastoris* host cells encoding said NAP;
(b) fermenting said host cells in a fermentation process that comprises a seed fermentation to grow host cells to a desired cell density and a production fermentation process that comprises in sequential order glycerol batch fermentation, glycerol fed-batch fermentation, methanol adaptation fermentation, and methanol induction fermentation, for up to about seven days, wherein the temperature of the methanol adaptation fermentation is maintained at about 28 ±2° C. for about the first four hours and at about 25±1° C. for the remainder of the methanol adaptation fermentation and the pH is maintained at about 2.9±0.1 during the methanol adaptation fermentation and the methanol induction fermentation;
(c) recovering NAP from said fermented host cells in a recovery process that comprises cation exchange expanded bed chromatography to separate NAP from cells and cellular debris, wherein the cation exchange expanded bed chromatography is performed at a pH of about 3.2.±0.2; and
(d) purifying NAP from the separated NAP from step (c) in a purification process comprising:
(i) performing hydrophobic interaction chromatography at about pH 3.0±0.1;
(ii) collecting NAP fractions from said hydrophobic interaction chromatography;
(iii) performing at least one ultrafiltration/diafiltration (UF/DF) on the NAP fractions to provide a NAP solution;
(iv) performing anion exchange chromatography on the NAP solution;
(v) collecting fractions containing NAP from the anion exchange chromatography; and
(vi) performing at least one UF/DF of NAP fractions from the anion exchange chromatography.

24. The process of claim 23, wherein the NAP is rNAPc2.

25. The process of claim 23, wherein the NAP is rNAPc2/proline.

* * * * *

SEQUENCE LISTING

<160> NUMBER OF SEQ ID NOS: 4

<210> SEQ ID NO 1
<211> LENGTH: 28
<212> TYPE: DNA
<213> ORGANISM: Ancyclostoma caninum
<220> FEATURE:
<221> NAME/KEY: misc_feature
<223> OTHER INFORMATION: Oligonucleotide primer

<400> SEQUENCE: 1
gcgtttaaag caacgatgca gtgtggtg             28

<210> SEQ ID NO 2
<211> LENGTH: 46
<212> TYPE: DNA
<213> ORGANISM: Ancyclostoma caninum
<220> FEATURE:

-continued

```
<221> NAME/KEY: misc_feature
<223> OTHER INFORMATION: Oligonucleotide primer

<400> SEQUENCE: 2
cgctctagaa gcttcatggg tttcgagttc cgggatatat aaagtc            46

<210> SEQ ID NO 3
<211> LENGTH: 84
<212> TYPE: PRT
<213> ORGANISM: Ancyclostoma caninum

<400> SEQUENCE: 3

Lys Ala Thr Met Gln Cys Gly Glu Asn Glu Lys Tyr Asp Ser Cys Gly
1               5                   10                  15

Ser Lys Glu Cys Asp Lys Cys Lys Tyr Asp Gly Val Glu Glu Glu
            20                  25                  30

Asp Asp Glu Glu Pro Asn Val Pro Cys Leu Val Arg Val Cys His Gln
        35                  40                  45

Asp Cys Val Cys Glu Glu Gly Phe Tyr Arg Asn Lys Asp Lys Cys
    50                  55                  60

Val Ser Ala Glu Asp Cys Glu Leu Asp Asn Met Asp Phe Ile Tyr Pro
65                  70                  75                  80

Gly Thr Arg Asn

<210> SEQ ID NO 4
<211> LENGTH: 85
<212> TYPE: PRT
<213> ORGANISM: Ancyclostoma caninum

<400> SEQUENCE: 4

Lys Ala Thr Met Gln Cys Gly Glu Asn Glu Lys Tyr Asp Ser Cys Gly
1               5                   10                  15

Ser Lys Glu Cys Asp Lys Cys Lys Tyr Asp Gly Val Glu Glu Glu
            20                  25                  30

Asp Asp Glu Glu Pro Asn Val Pro Cys Leu Val Arg Val Cys His Gln
        35                  40                  45

Asp Cys Val Cys Glu Glu Gly Phe Tyr Arg Asn Lys Asp Lys Cys
    50                  55                  60

Val Ser Ala Glu Asp Cys Glu Leu Asp Asn Met Asp Phe Ile Tyr Pro
65                  70                  75                  80

Gly Thr Arg Asn Pro
                85
```